(12) United States Patent
Haam et al.

(10) Patent No.: US 9,320,809 B2
(45) Date of Patent: Apr. 26, 2016

(54) NANOPARTICLE COMPRISING HYDROPHOBIC DRUG CONJUGATED TO CATIONIC POLYMER AND HYDROPHILIC DRUG CONJUGATED TO ANIONIC POLYMER

(71) Applicant: University-Industry Foundation, Yonsei University, Seoul (KR)

(72) Inventors: Seungjoo Haam, Seoul (KR); Yong-min Huh, Seoul (KR); Ilkoo Noh, Seoul (KR); Jihye Choi, Incheon (KR); Hyun-Ouk Kim, Seoul (KR); Dayeon Yun, Seoul (KR)

(73) Assignee: University-Industry Foundation, Yonsei University (KR)

( * ) Notice: Subject to any disclaimer, the term of this patent is extended or adjusted under 35 U.S.C. 154(b) by 0 days.

(21) Appl. No.: 14/629,732

(22) Filed: Feb. 24, 2015

(65) Prior Publication Data

US 2016/0022824 A1 Jan. 28, 2016

(30) Foreign Application Priority Data

Jul. 24, 2014 (KR) ........................ 10-2014-0094169

(51) Int. Cl.
| | |
|---|---|
| *A61K 9/14* | (2006.01) |
| *A61K 9/51* | (2006.01) |
| *A61K 47/48* | (2006.01) |
| *A61K 31/7068* | (2006.01) |
| *A61K 31/337* | (2006.01) |

(52) U.S. Cl.
CPC ............ *A61K 47/4823* (2013.01); *A61K 31/337* (2013.01); *A61K 31/7068* (2013.01); *A61K 47/48315* (2013.01); *A61K 47/48776* (2013.01); *A61K 47/48238* (2013.01); *Y10S 977/773* (2013.01); *Y10S 977/906* (2013.01); *Y10S 977/911* (2013.01)

(58) Field of Classification Search
None
See application file for complete search history.

(56) References Cited

U.S. PATENT DOCUMENTS

| | | | |
|---|---|---|---|
| 2003/0073615 A1* | 4/2003 | Li et al. .............................. 514/2 |
| 2007/0197465 A1* | 8/2007 | Ikeya .................. A61K 47/4823 514/54 |

(Continued)

FOREIGN PATENT DOCUMENTS

KR 10-2010-0134398 12/2011

OTHER PUBLICATIONS

Z Dong, W Zheng, Z Xu, Z Yin. "Improved Stability and Tumor Targeting of 5-Fluorouracil by Conjugation with Hyaluronan." Journal of Applied Polymer Science, vol. 136 Issue 2, 2013, pp. 927-932 followed by 2 back pages (8 total sheets).*

(Continued)

*Primary Examiner* — Isaac Shomer
(74) *Attorney, Agent, or Firm* — Cooley LLP; Matthew Pavao

(57) ABSTRACT

The present invention relates to a nanoparticle including a hydrophobic drug conjugated to a cationic polymer and a hydrophilic drug conjugated to an anionic polymer, a method of preparing the same and a pharmaceutical use thereof. The nanoparticle according to an embodiment of the present invention may deliver the hydrophilic drug and the hydrophobic drug at the same time, and may control an initial drug burst. Further, the nanoparticle according to an embodiment of the present invention is specific to a cancer cell environment, and thus selective diagnosis or treatment of cancer cells is possible.

8 Claims, 22 Drawing Sheets

(56) References Cited

U.S. PATENT DOCUMENTS

2007/0292387 A1* 12/2007 Jon et al. ............... 424/85.1
2009/0011008 A1* 1/2009 Sung et al. ............. 424/451

OTHER PUBLICATIONS

STN Solubility Data. Obtained by examiner on Jul. 9, 2015. 128 pages.*

FA Oyarzun-Ampuero, FM Goycoolea, D Torres, MJ Alonso. "A new drug nanocarrier consisting of polyarginine and hyaluronic acid." European Journal of Pharmaceutics and Biopharmaceutics, vol. 79, 2011, pp. 54-57.*

Z Dong, W Zheng, Z Xu, Z Yin. "Improved Stability and Tumor Targeting of 5-Fluorouracil by Conjugation with Hyaluronan." Journal of Applied Polymer Science, vol. 130, 2013, pp. 927-932.*

"Proton-Dependent Multi-Drugs Release Using Self-Assembled Nanoparticles for the Induction of Biliary Cancer Cell Death" Polymer Science and Technology, Feb. 2014, vol. 25, No. 1 (English Abstract Provided).

Wang et al., "Enhanced Anti-Tumor Efficavy by Co-Delivery of Doxorubicin and Paclitaxel With Amphiphilic Methoxy PEG-PLGA Copolymer Nanparticles", Biomaterials 32:9291-8290 (2011).

Patel et al., "Chitosan Mediated Targeted Drug Delivery System: A Review", J. Pharm Pharmaceutical Sci. 13(3):536-557, (2010).

Goodarzi et al., "CD44-Targeted Docetaxel Conjugate for Cancer Cells and Cancer Stem-Like Cells: A Novel Hyaluronic Acid-Based Drug Delivery System", Chemical Biology & Drug Design, 83(6):741-752, (2014).

Nitta et al., "Biopolymer-Based Nanoparticles for Drug/Gene Delivery and Tissue Engineering", Int. J. Mol. Sci. 14:1629-1654, (2013).

\* cited by examiner

NANOPARTICLE COMPRISING HYDROPHOBIC DRUG CONJUGATED TO CATIONIC POLYMER AND HYDROPHILIC DRUG CONJUGATED TO ANIONIC POLYMER

The present application claims priority to KR application 10-2014-0094169 filed Jul. 24, 2014, which is hereby incorporated in its entirety including all tables, figures, and claims.

The present invention relates to a nanoparticle including a hydrophobic drug conjugated to a cationic biocompatible polymer and a hydrophilic drug conjugated to an anionic biocompatible polymer, a method of preparing the same and a pharmaceutical use thereof.

INCORPORATION-BY-REFERENCE OF SEQUENCE LISTING

The contents of the text file named "G14U16C0827-sequenceST25.txt", which was created on Feb. 24, 2015 and is 2 KB in size, are hereby incorporated by reference in their entirety.

BACKGROUND OF INVENTION

In existing drug delivery systems, a hydrophobic drug or a hydrophilic drug has been generally supported on a vehicle such as a liposome, a polymersome, or the like to be delivered. In the case of such delivery systems, a target-specific function is required to be provided to deliver a drug to a desired site, and thus a separate process of conjugating a ligand or the like performing a target-specific function is required (Korean patent application No. 2009-0052964 (Jun. 15, 2009).

However, a drug delivery system in which a hydrophilic drug and a hydrophobic drug may be delivered at the same time, target-specific properties may be provided without a separate process and an initial drug burst may be suppressed has yet to be reported.

BRIEF SUMMARY OF THE INVENTION

The present invention is directed to providing a nanoparticle capable of delivering a hydrophilic drug and a hydrophobic drug at the same time, and controlling an initial drug burst by conjugating the hydrophobic drug and the hydrophilic drug to a cationic polymer and an anionic polymer, respectively.

One aspect of the present invention provides a drug complex including an anionic biocompatible polymer, and a hydrophilic drug conjugated to the anionic biocompatible polymer.

Another aspect of the present invention provides a nanoparticle including a hydrophobic drug conjugated to a cationic biocompatible polymer and a hydrophilic drug conjugated to an anionic biocompatible polymer, and forming a self-assembly by a balance between a cation and an anion.

Still another aspect of the present invention provides a method of preparing the nanoparticle including reacting a hydrophobic drug conjugated to a cationic biocompatible polymer and a hydrophilic drug conjugated to an anionic biocompatible polymer.

The nanoparticle according to the embodiment of the present invention may deliver the hydrophilic drug and the hydrophobic drug at the same time, and may control an initial drug burst.

Further, the nanoparticle according to the embodiment of the present invention is specific to a cancer cell environment, and thus selective diagnosis or treatment of cancer cells is possible.

BRIEF DESCRIPTION OF THE DRAWINGS

FIG. 3a shows a size of the nanoparticle according to a ratio HA-GEM:PLL-PTX, and FIG. 3b shows a zeta potential according to the ratio HA-GEM:PLL-PTX. FIG. 3c shows a result of an observation of AFM of the nanoparticle according to the ratio HA-GEM:PLL-PTX.

FIG. 5a shows the result of the observation through a confocal microscope, FIG. 5b shows the result of the measurement of fluorescence intensity of rhodamine B, FIG. 5c shows the result of analysis of an amount of over-expression of CD44 in HuCCT1 and SCK, and FIG. 5d shows relative intensity of rhodamine B for each test group based on FIG. 5b.

FIG. 8a shows a change in a size of the cancer in mice to which a HuCCT1 cell was transplanted according to each drug treatment group. FIG. 8b shows changes in weights of the mice during the test. FIG. 8c shows the result of the measurement of the weight of the cut cancer tissue, and FIG. 8d shows the size of the cut cancer tissue. FIG. 8e shows the result of histological analysis through H&E dyeing.

DETAILED DESCRIPTION OF THE INVENTION

Figure 1A:
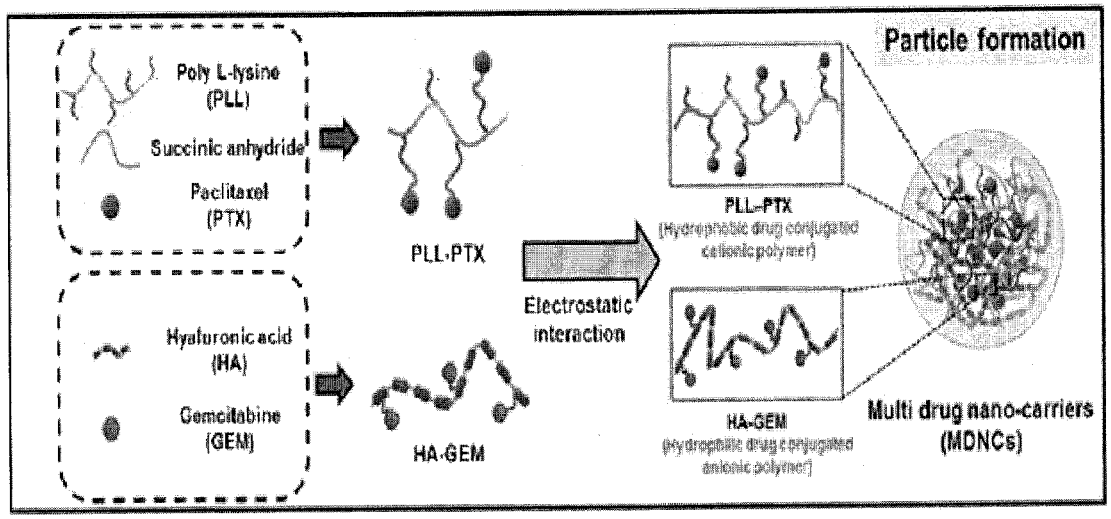
FIG. 1a is a schematic view of a composition of a nanoparticle according to an embodiment of the present invention.

Hereinafter, the composition according to an embodiment of the present invention will be described in detail.

One aspect of the present invention provides a drug complex including an anionic biocompatible polymer, and a hydrophilic drug conjugated to the anionic biocompatible polymer.

In the embodiment, the hydrophilic drug may be one or more selected from the group consisting of busulfan, chlorambucil, cyclophosphamide, melphalan, cisplatin, ifosfamide, cytarabine, 5-fluorouracil (5-FU), methotrexate (MTX), actinomycin D, bleomycin and gemcitabine.

In the embodiment, the anionic biocompatible polymer may have a hydroxyl group or a carboxyl group. The anionic biocompatible polymer may be one or more selected from the group consisting of heparins, carboxymethyl cellulose, dermatan sulfate, dextran, alginate, chondroitin sulfate and hyaluronic acids.

In a specific embodiment, a bond between a biocompatible polymer and a drug may be an ester bond, an imine bond, a hydrazone bond, an acetal bond or a cyclic acetal bond.

In an embodiment, the drug complex according to the embodiment of the present invention may include a unit of the following Formula 1.

P-L-H [Formula 1]

where P is an anionic biocompatible polymer having a hydroxyl group or a carboxyl group, L is an organic linker selected from the group consisting of —C(O)—O—, —C=N—NH—, —CH=N— and —O—CH$_2$—O—, and H refers to a residue of a hydrophilic drug.

A drug complex including an anionic biocompatible polymer, and a hydrophilic drug conjugated to the anionic biocompatible polymer enters a cell through receptor-mediated endocytosis with respect to a cancer-cell-specific marker, an ester bond, an imine bond, a hydrazone bond, an acetal bond or a cyclic acetal bond in the cell is specifically degraded in a specific bio-environment to break a bond between the hydrophilic drug and the polymer in the specific bio-environment, and thereby the hydrophilic drug may be delivered in the cell.

Another aspect of the present invention provides a nanoparticle including a hydrophobic drug conjugated to a cationic biocompatible polymer and a hydrophilic drug conjugated to an anionic biocompatible polymer, and forming a self-assembly by a balance between a cation and an anion.

In the embodiment, a bond between a biocompatible polymer and a drug may be an ester bond, an imine bond, a hydrazone bond, an acetal bond or a cyclic acetal bond. For example, the cationic biocompatible polymer and the anionic biocompatible polymer may be respectively conjugated to the hydrophobic drug and the hydrophilic drug through an ester bond.

Further, after the nanoparticle according to the embodiment of the present invention enters the cell through receptor-mediated endocytosis with respect to a cancer-cell-specific marker, an ester bond, an imine bond, a hydrazone bond, an acetal bond or a cyclic acetal bond in a particle is specifically degraded in a specific bio-environment, a self-assembly is degraded in the specific bio-environment, and thereby the hydrophilic drug and the hydrophobic drug may be delivered into the cell at the same time. Accordingly, the nanoparticle according to the embodiment of the present invention may be used as a drug carrier for diagnosis or treatment.

The composition of the nanoparticle according to the embodiment of the present invention is illustrated in FIG. 1.

Figure 1B:
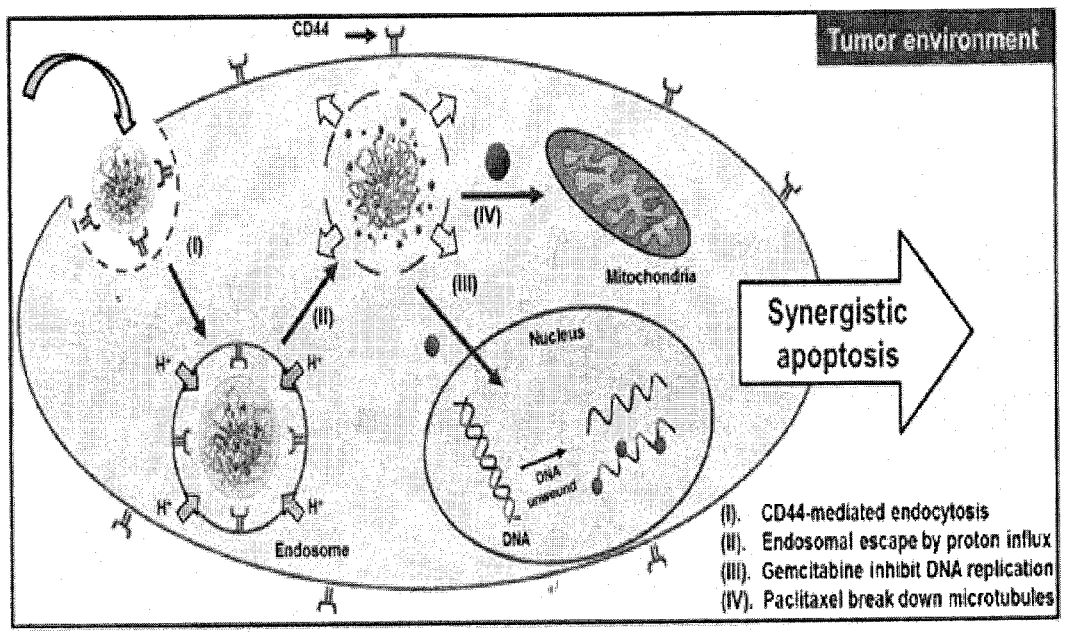
FIG. 1b is a schematic view illustrating a drug release process in cancer cells.

Multi drug nano carriers (MDNCs) according to the embodiment of the present invention in which a complex conjugated to a cationic biocompatible polymer and a hydrophobic drug, and a complex conjugated to an anionic biocompatible polymer and a hydrophilic drug are self-assembled by mutual electrostatic attraction between a cation and an anion are formed (FIG. 1a). MDNCs enter a cancer cell through CD44-mediated endocytosis in a living body, a bond between a drug and a polymer is degraded in a cancer-cell-specific environment, and thereby the drug is released (FIG. 1b). For example, when the bond between the drug and the polymer is an ester bond, a degradation speed of the ester bond is increased by protons (H+) at a pH in a range of 5.0 to 5.5 in the cancer cell. As the ester bond is degraded, the nanoparticle disintegrates, and thereby the hydrophilic drug and the hydrophobic drug included in the nanoparticle may be released. An inactive state of the drug which is conjugated to the biocompatible polymer turns to an active state, the initial drug burst may be controlled, and effective cancer cell death may be achieved.

In the embodiment of the present invention, any biocompatible polymer which is cationic may be used as the cationic biocompatible polymer without limitation. In the embodiment, the cationic biocompatible polymer may be a chitosan or a polymer of base amino acids, and for example, may be one or more selected from the group consisting of polylysin, polyhistidine and polyarginine. For example, the cationic biocompatible polymer may be a lysine homopolymer having a molecular weight in the range of 2 to 40 K.

Further, the cationic biocompatible polymer may be represented by the following Formula 2.

(poly-M)$_k$ [Formula 2]

where M is lysine, histidine or arginine, and k is a number in a range of 2 to 50.

Any polymer which is anionic and biocompatible may be used as the anionic biocompatible polymer without limitation. In the embodiment, the anionic biocompatible polymer may be one or more selected from the group consisting of heparins, hyaluronic acids, carboxymethyl cellulose, dermatan sulfate, dextran, alginate, chondroitin sulfate and hyaluronic acids. For example, the anionic biocompatible polymer may be hyaluronic acid having a molecular weight in the range of 10 to 100 K.

In the embodiment, hydrophobic drug may be, but is not limited to, one or more selected from the group consisting of vinblastine, etoposide, actinomycin D, bleomycin, methotrexate, an alkylating compound, alkeran, cisplatinum, cytoxan, daunorubicin, hydrea, ifosfamide, mithramycin, mitomycin, mitoxantrone, nitrogen mustard, velban, vincristine, carboplatinum, idarubicin, irinotecan, leustatin, navelbine, taxotere, topotecan, adriamycin, cisplatin, daunomycin, 5-fluorouracil and paclitaxel.

In the embodiment, the hydrophilic drug may be one or more selected from the group consisting of busulfan, chlorambucil, cyclophosphamide, melphalan, cisplatin, Ifosfamide, cytarabine, 5-fluorouracil (5-FU), methotrexate (MTX), actinomycin D, bleomycin and gemcitabine.

Further, a fluorescent material may be further added to the nanoparticle according to the embodiment of the present invention, and used for a cancer diagnosis. The fluorescent material may be physicochemically enclosed or conjugated in a hydrophilic area. The fluorescent material may be a fluorescent body which emits fluorescent light in a visible light area or a near infrared light area, and for example, fluorescein, BODIPY, tetramethylrhodamine, Alexa, cyanine, allopicocyanine or a fluorescent material emitting another fluorescent light may be used as the fluorescent material. Further, a fluorescent material having a high quantum yield may be used. Further, the fluorescent material may be a hydrophilic dye.

In the embodiment, an average diameter of the nanoparticle may be in the range of 100 to 300 nm. In the above-described range, the nanoparticle may be effectively delivered to a desired site, minimizing bio-stimulation.

In the embodiment, a weight ratio between the hydrophobic drug conjugated to the cationic biocompatible polymer to the hydrophilic drug conjugated to the anionic biocompatible polymer may be in the range of 1:70 to 70:1, 1:50 to 50:1, 1:35 to 35:1, 1:20 to 20:1, 1:20 to 1:50, 1:20 to 1:40, 1:25 to 1:35, or 1:30 to 1:35. For example, a weight ratio between the hydrophobic drug conjugated to the cationic biocompatible polymer through an ester bond to the hydrophilic drug conjugated to the anionic biocompatible polymer through an ester bond may be in the range of 1:25 to 1:35 or 1:30 to 1:35. When the hydrophobic drug is paclitaxel and the hydrophilic drug is gemcitabine, the nanoparticle prepared in the above-described weight ratio has a small diameter, is smoothly spherical, and has a high polydispersity index (Experimental Example 1).

Still another aspect of the present invention provides method of preparing the nanoparticle, including reacting the hydrophobic drug conjugated to the cationic biocompatible polymer and the hydrophilic drug conjugated to the anionic biocompatible polymer. When the hydrophobic drug conjugated to the cationic biocompatible polymer and the hydrophilic drug conjugated to the anionic biocompatible polymer are mixed and vortexed, the nanoparticle forming a self-assembly according to mutual electrostatic attraction between a cation and an anion may be prepared.

In the embodiment, a bond between a biocompatible polymer and a drug may be an ester bond, an imine bond, a hydrazone bond, an acetal bond or a cyclic acetal bond.

For example, the hydrophobic drug conjugated to the cationic biocompatible polymer through an ester bond may be prepared by modifying the hydrophobic drug to have a functional group capable of bonding to the cationic polymer having a primary amine group, and then reacting the modified hydrophobic drug with the cationic polymer having a primary amine group. For example, the functional group capable of bonding to the cationic polymer having a primary amine group may be, but is not limited to, succinic anhydride (SA), glutaric anhydride, succinyl chloride or glutaryl chloride. A method of introducing succinic anhydride into the hydrophobic drug is well known in the related field, and well-known methods may be used without limitation. For example, paclitaxel, succinic anhydride and 4-dimethylaminopyridine are put into a pyridine solution and reacted, and thereby paclitaxel to which succinic anhydride is introduced may be prepared (Example 1).

The hydrophilic drug conjugated to the anionic biocompatible polymer through an ester bond, for example, may be prepared by reacting the anionic biocompatible polymer having a carboxyl group with the hydrophilic drug having a hydroxyl group (Example 1).

When the prepared hydrophobic drug conjugated to the cationic biocompatible polymer through an ester bond and hydrophilic drug conjugated to the anionic biocompatible polymer through an ester bond are mixed and vortexed, the nanoparticle forming a self-assembly according to mutual electrostatic attraction between a cation and an anion may be prepared.

Still another aspect of the present invention provides a pharmaceutical use of the drug complex and the nanoparticle. The drug complex or the nanoparticle according to the embodiment of the present invention may be used as a pharmaceutical composition for diagnosis and treatment of cancer. Further, when the drug complex or the nanoparticle according to the embodiment of the present invention is administered to an individual, cancer may be diagnosed or treated. Accordingly, one aspect of the present invention provides a method of treating cancer including administering the drug complex or the nanoparticle to a subject.

For example, hyaluronic acids are specific to CD44 which is a cell surface protein, and thus the nanoparticle according to the embodiment of the present invention is specific to a cancer cell in which CD44 is over-expressed without a separate ligand for target-specific properties. Accordingly, any type of cancer in which CD44 is over-expressed may be used as cancer to which the nanoparticle according to the embodiment of the present invention may be applied without limitation. For example, the cancer may be pancreatic cancer, liver cancer, breast cancer, lung cancer, stomach cancer, rectal cancer, gallbladder cancer, ovarian cancer, bladder cancer, colon cancer, lymphoma, brain cancer, uterine cancer, prostate cancer and a malignant melanoma or biliary tract cancer, but is not limited thereto.

In order to determine whether the nanoparticle according to the embodiment of the present invention enters a CD44-over-expressed cell well, a comparison experiment was performed using a CD44-over-expressed cell strain and a CD44-low-expressed cell strain. As a result, the nanoparticle according to the embodiment of the present invention could be determined to enter the CD44-over-expressed cell strain more effectively than the CD44-low-expressed cell strain, and to have an excellent cytotoxic effect (Experimental Examples 3 and 4).

Further, the nanoparticle according to the embodiment of the present invention is degraded in a specific environment in the cancer cell. The cancer cell generates a large amount of pyruvic acids, lactic acids, or the like, thereby causing pH in the cancer cells to be in the acidic range of 5.0 to 5.5. The ester bond is degraded by protons (H+) at pH in the above-described range of 5.0 to 5.5, the nanoparticle according to the embodiment of the present invention is specifically degraded, and thereby the hydrophilic drug and the hydrophobic drug are released. That is, the nanoparticle according to the embodiment of the present invention only releases the drug in a cancer-cell-specific environment (Experimental Example 2).

The pharmaceutical composition for cancer diagnosis and treatment according to the embodiment of the present invention may further include a pharmaceutically acceptable carrier. The pharmaceutically acceptable carrier includes a carrier and a vehicle which are typically used in the pharmaceutical field, and specifically, includes an ion exchange resin, alumina, aluminum stearate, lecithin, blood serum protein (e.g. human serum albumin), a buffer material (e.g. phosphates, glycine, sorbic acid, potassium sorbate, a partial glyceride mixture of saturated plant fatty acids), water, salts or electrolytes (e.g. protamine sulfate, disodium hydrogen phosphate, potassium hydrogen phosphate, sodium chloride, and salts of zinc), colloidal silica, magnesium trisilicate, polyvinylpyrrolidone, a cellulose-based substrate, polyethylene glycol, sodium carboxymethylcellulose, polyarylate, wax, polyethylene glycol, and wool grease, but the present invention is not limited thereto.

Further, the pharmaceutical composition for cancer diagnosis and treatment according to the embodiment of the present invention may further include a lubricant, wetting agent, emulsifier, suspending agent, or preserving agent in addition to the above components.

When the drug complex or the nanoparticle according to the embodiment of the present invention further includes a fluorescent material, the nanoparticle may have a contrast effect, and thus treatment and diagnosis of cancer may be performed at the same time. The fluorescent material may be physicochemically enclosed or conjugated in the nanoparticle. The fluorescent material may be a fluorescent body which emits fluorescent light in a visible light or near infrared light range, and for example, fluorescein, BODIPY, tetramethylrhodamine, Alexa, cyanine, allopicocyanine or a fluorescent material emitting another fluorescent light may be used as the fluorescent material. Further, a fluorescent material having a high quantum yield may be used. Further, the fluorescent material may be a hydrophilic dye.

In the embodiment, when the drug complex or the nanoparticle according to the embodiment of the present invention is used as a contrast agent for diagnosis, the contrast agent may be prepared as an aqueous solution for parenteral administration, and preferably, a buffer solution, such as a Hank's solution, a Ringer's solution, or physically buffered saline water may be used. A substrate which may increase viscosity of an aqueous injection suspension, such as sodium carboxymethylcellulose, sorbitol, or dextran may be added to the suspension.

Further, the contrast agent according to the embodiment of the present invention may be in the form of a formulation for sterile injection, such as an aqueous or oil suspension for sterile injection. The suspension may be formulated according to well-known technologies in the related field using a suitable dispersant or wetting agent (e.g. Tween 80) and suspending agent.

Further, the formulation for sterile injection may also be a solution or suspension (e.g. a solution in 1,3-butanediol) for sterile injection in a non-toxic diluent or a solvent allowed for parenteral use. Examples of vehicles and solvents which may be used include mannitol, water, a Ringer's solution, and an isotonic sodium chloride solution. Further, sterile non-volatile oil is usually used as a solvent or suspending medium. Any type of non-volatile and non-irritant oil, including synthetic mono- and di-glycerides, may be used for the above-described purpose.

The contrast agent according to the embodiment of the present invention may be used to obtain images by administering the contrast agent to the tissue or cell separated from a subject to be diagnosed and then sensing a signal released from the nanoparticle.

In order to sense the signal released from the nanoparticle, a magnetic resonance imaging (MRI) device and optical imaging are preferably used.

Hereinafter, the present invention will be described in detail in conjunction with examples and experimental examples. The following examples and experimental examples are merely examples of the present invention, and the scope of the present invention is not intended to be limited to thereto.

EXAMPLES

Example 1

Preparation of Nanoparticle Including Hydrophobic Drug Conjugated to Cationic Polymer and Hydrophilic Drug Conjugated to Anionic Polymer Example 1-1

Preparation of Nanoparticle of Hydrophobic Drug Conjugated to Cationic Polymer

In order to polymerize a cationic polymer having a primary amine group an, Lys (Z) having a protected carboxybenzyl (CBZ) group was reacted for 3 hours at 50° C. in a tetrahydrofuran solvent. After 3 hours, Lys (Z) was deposited in a hexane, and thereby Lys (Z)-NCA was obtained. The generated Lys (Z)-NCA was dissolved in an N,N'-dimethyl formamide solution from which water was removed, and then a hexylamine which is a primary amine was put therein such that the ratio of the hexylamine to the Lys (Z)-NCA was 1:30. The mixed solution was reacted for 48 hours at 35° C., and then was deposited in an ether to obtain poly-L-lysine (PLL) (Z). As a result of GPC analysis, it could be determined that a molecular weight of a polymer was 4525, and a polydispersity index (PDI) of the polymer was 1.0685.

In order to activate the primary amine group, after PLL (Z) was dissolved in trifluoreacetic acid, HBr at an amount of three times the mole ratio of a protecting group was put into the PLL (Z), and then was reacted at room temperature for 2 hours. After the reaction was complete, PLL (Z) was deposited in the ether, and then was refined using a dialysis tube (molecular weight cut-off of 1000) for two days to remove impurities. After the refinement, water was removed by lyophilization to obtain pure PLL.

In order to form a functional group which may be conjugated to PLL in paclitaxel (PTX), PTX, succinic anhydride (SA) and 4-dimethylaminopyridine (DMAP) were put into a pyridine solution, and then were reacted for 3 hours. After 3 hours, the reaction solution was mixed with dichloromethane such that a volume ratio therebetween was 1:1, the reaction solution was put into a separatory funnel with water, and thereby a remaining material after the reaction was removed. A solution obtained from the separatory funnel was deposited in a hexane to obtain PTX-SA.

In order to bond the PTX-SA obtained as a product to PLL, after PTX-SA was dissolved in a DMSO solution, a carboxyl group was activated at room temperature for 1 hour using N,N'-dicyclohexylcarbodiimide (DCC) and N-hydroxysuccinimide (NHS). After 1 hour, the solution was mixed with a PLL solution dissolved in DMSO/DIW (a volume ratio of 4:1), and then the mixed solution was reacted at room temperature for 24 hours. After the reaction, the reaction solution was mixed in 70% methanol, was refined using amicon (molecular weight: 3000), and then was lyophilized to obtain PLL-PTX (refer to (a) in Scheme 1).

Figure 2A:
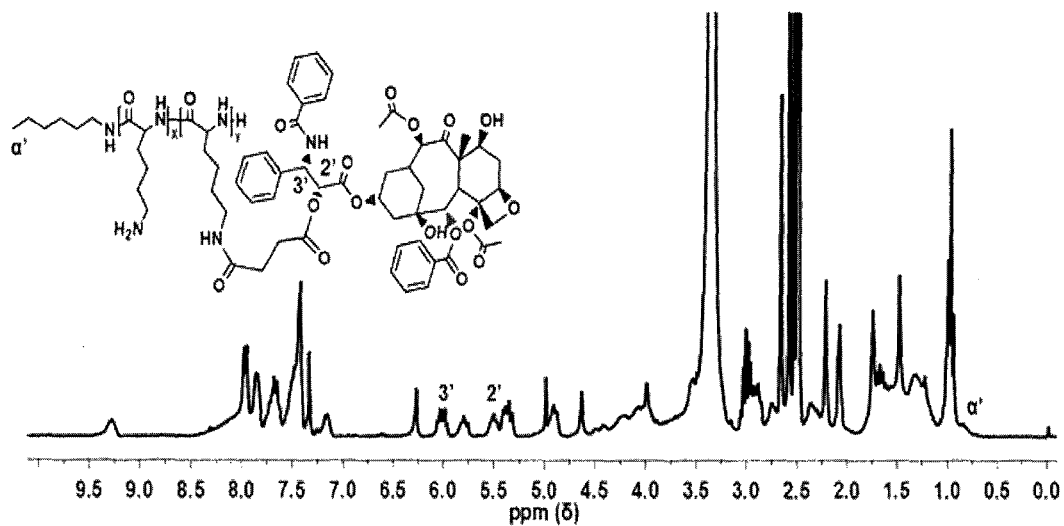
FIG. 2a illustrates a result of analysis of NMR data of PLL-PTX.

A result of analyzing the PLL-PTX obtained as described above using NMR is shown in FIG. 2(a). In FIG. 2(a), α, α', 1', 2', 3', 5' and 6' in a chemical structure correspond to α, α', 1', 2', 3', 5' and 6' in NMR data.

Example 1-2

Preparation of Nanoparticle Including Hydrophilic Drug Conjugated to Anionic Polymer In order to bond hyaluronic acid (HA) as an anionic polymer and gemcitabine (GEM) which is a hydrophilic drug, HA was dialyzed in a diluted acid, Na+ which was conjugated to HA by an ionic bond was removed, and then HA was lyophilized. After the lyophilized material and GEM were mixed in DMSO, DCC and DMAP were put therein, and then a carboxyl acid of HA and a hydroxyl group of GEM were reacted at 40° C. for 24 hours. After the reaction was complete, the reaction solution was deposited in methanol to obtain HA-GEM (refer to (b) in Scheme 1).

Figure 2B:
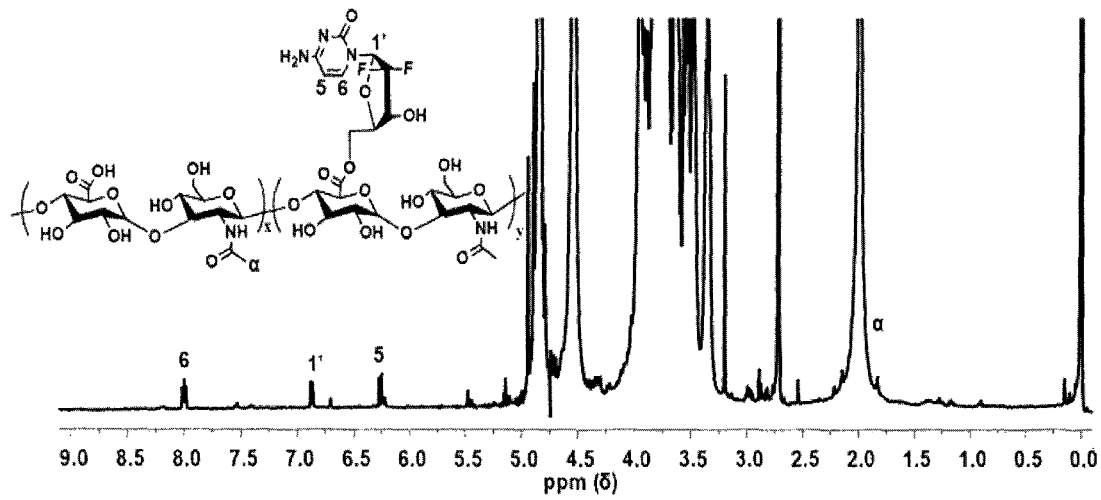
FIG. 2b shows the result of analysis of NMR data of HA-GEM. α, α', 1', 2', 3', 5 and 6 in a chemical structure correspond to α, α', 1', 2', 3', 5 and 6' in NMR data, respectively.

A result of analyzing the HA-GEM obtained as described above using NMR is shown in FIG. 2(b). In FIG. 2(b), α, α', 1', 2', 3', 5 and 6 in a chemical structure are represented by α, α', 1', 2', 3', 5 and 6' in NMR data.

Example 1-3

Preparation of Nanoparticle Including Hydrophobic Drug Conjugated to Cationic Polymer and Hydrophilic Drug Conjugated to Anionic Polymer PLL-PTX prepared in Example 1-1 and HA-GEM prepared in Example 1-2 were put into HEPES buffer having a concentration of 10 mM (pH 7.4) by changing the weight ratio (HA-GEM:PLL-PTX=1:1, 2:1, 4:1, 8:1, 16:1, 32:1 and 64:1), mixed, and then vortexed for 30 minutes. Then, the mixed solution was incubated at 4° C. for 3 hours, and thereby multi-drug nano-carriers (MDNCs) were prepared. A preparation process of the MDNCs is shown in the following Scheme 1.

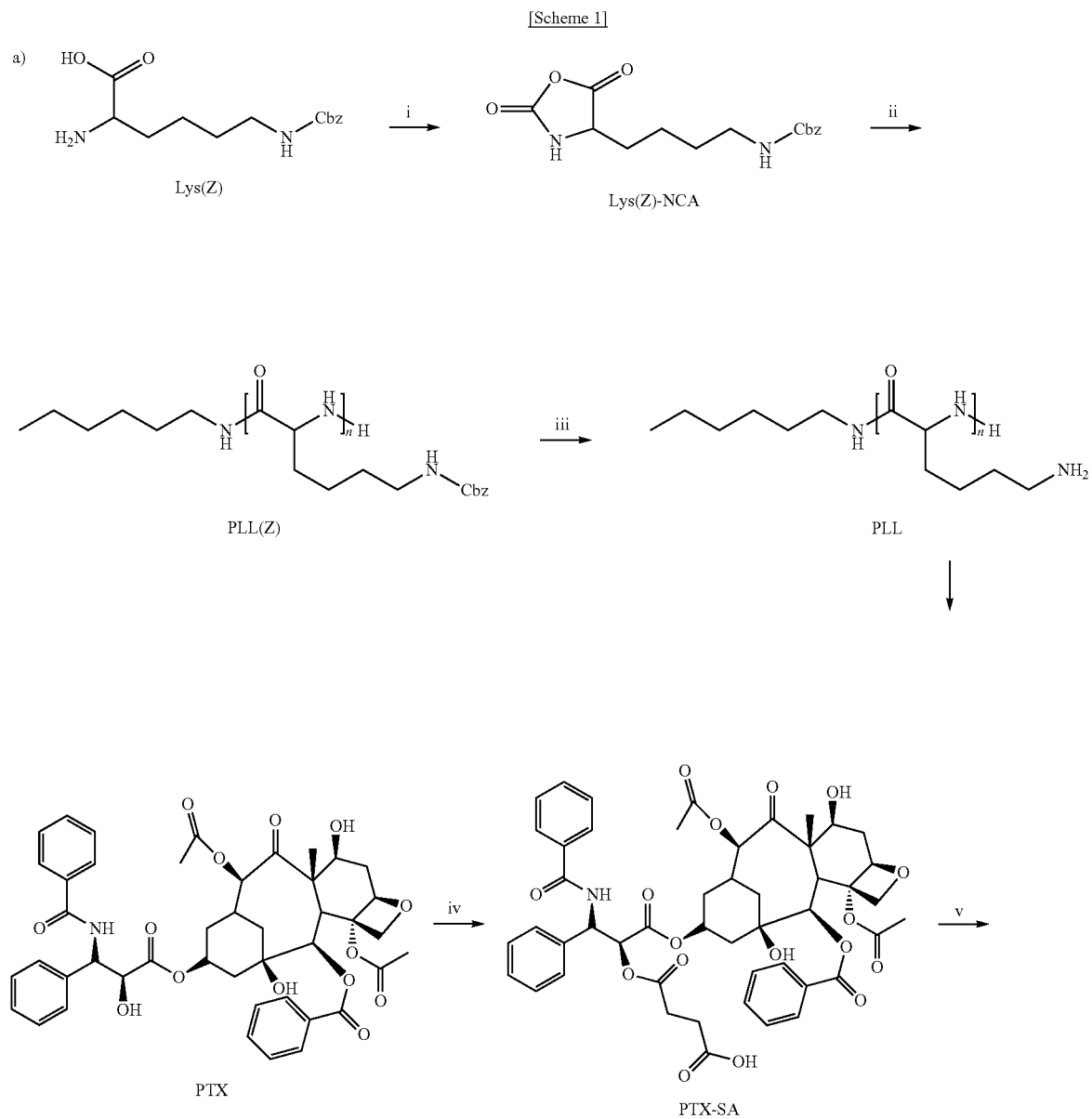

[Scheme 1]

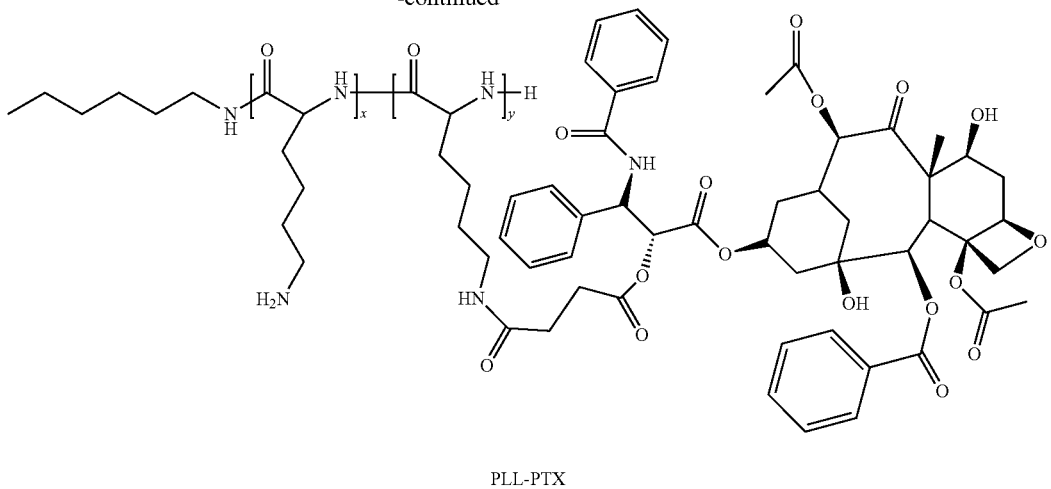

PLL-PTX

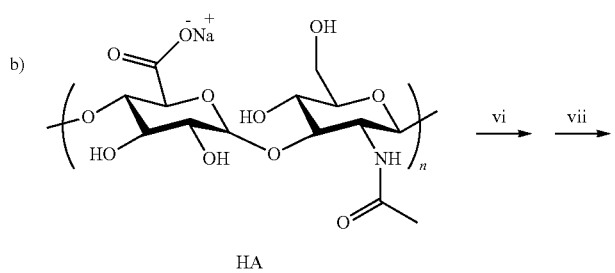

HA

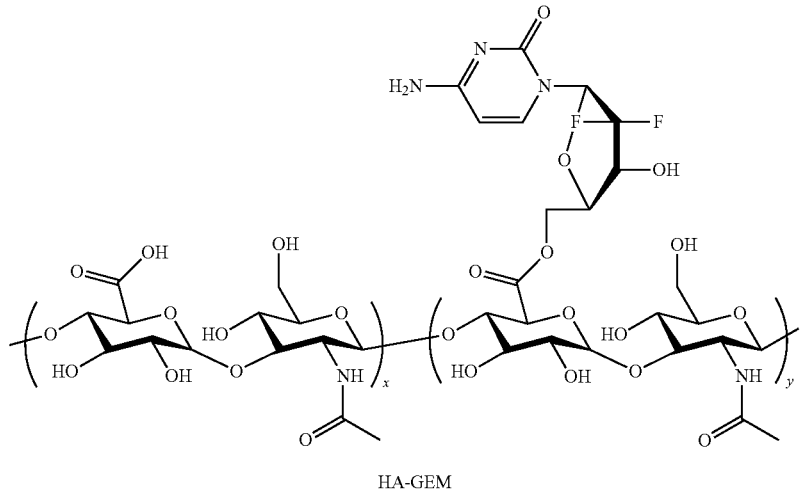

HA-GEM

Experimental Example 1

Analysis of Physical Properties of Nanoparticle

Figure 3A:
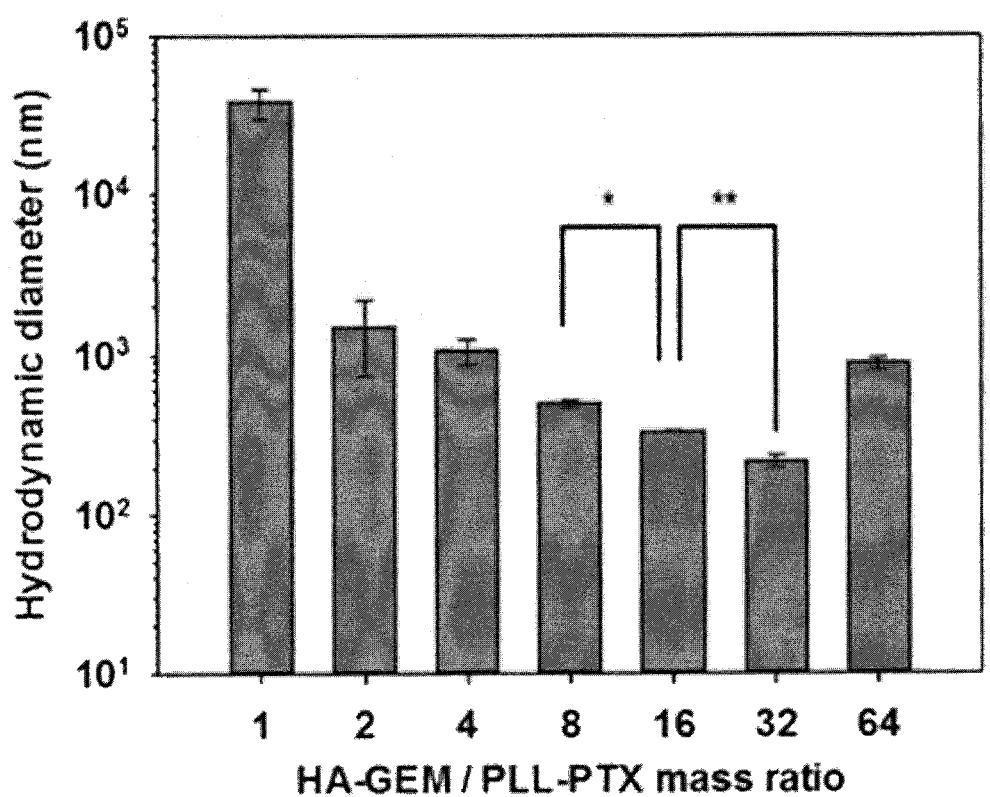
FIG. 3a, FIG. 3b and FIG. 3c illustrate the results of analysis of physical properties of MDNCs. Specifically.
Figure 3B:
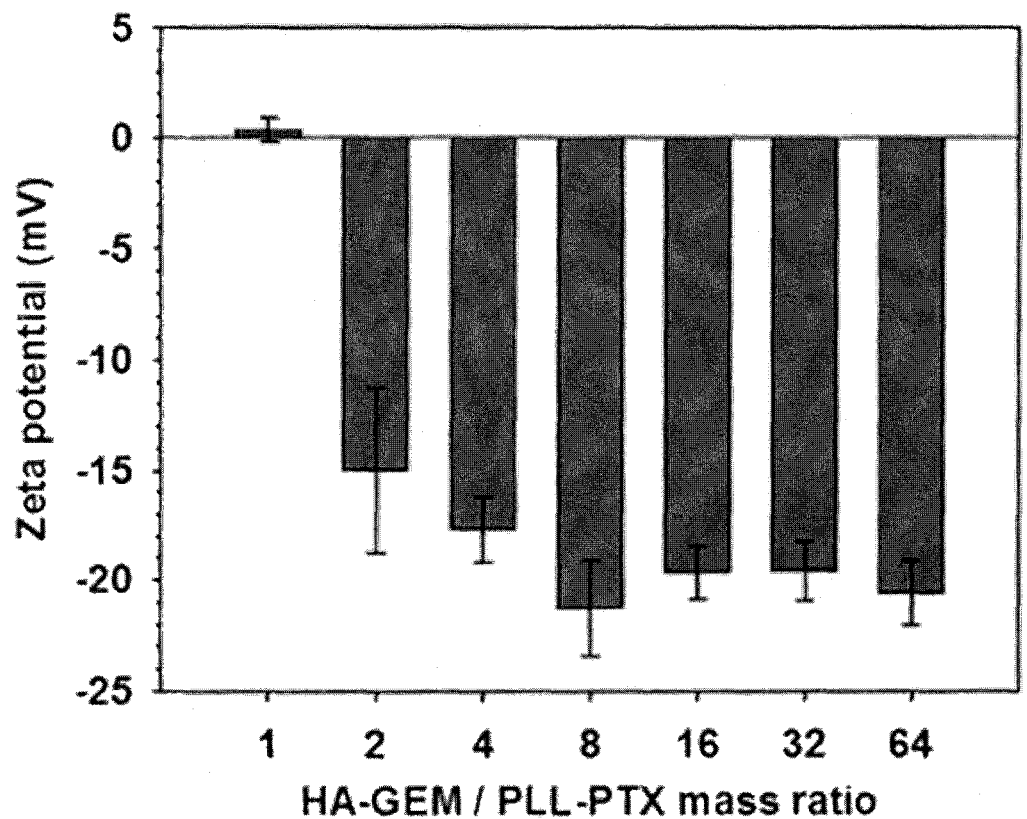
Figure 3C:
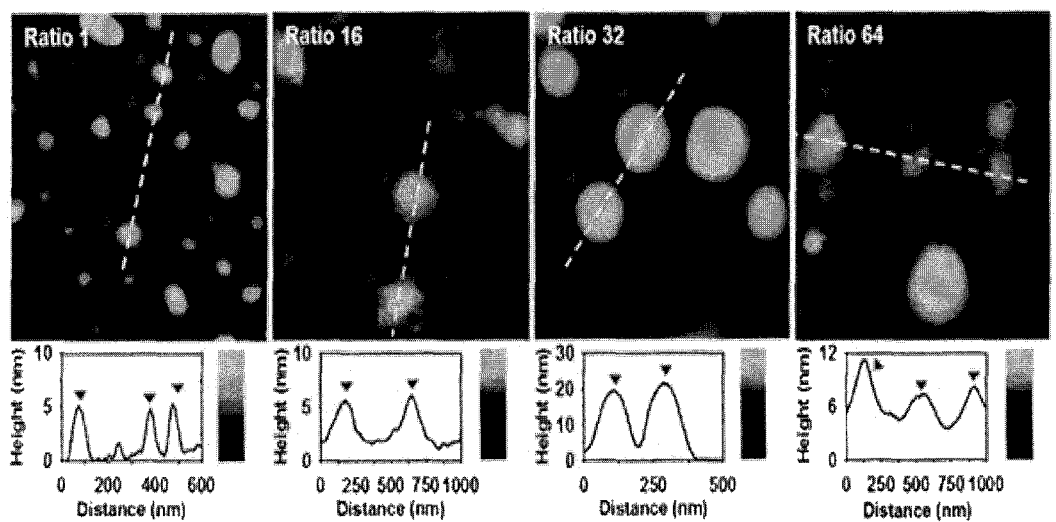

Physical properties of the MDNCs prepared in Example 1 were analyzed. As illustrated in FIG. 3(a), when a mass ratio between HA-GEM and PLL-PTX was 32:1, a particle diameter of the nanoparticle was determined to be smallest. As illustrated in FIG. 3(b), when a mass ratio between HA-GEM and PLL-PTX was 8:1 or more, a zeta potential was determined to be maintained at −20 mV. As illustrated in FIG. 3(c), as a result of an AFM observation, when the mass ratio between HA-GEM and PLL-PTX was 32:1, it was determined that the nanoparticle was smoothly spherical, and had the highest polydispersity index. That is, these results denote that physical properties of the nanoparticle prepared with the mass ratio between HA-GEM to PLL-PTX of 32:1 were most excellent.

Experimental Example 2

Determination of In Vitro Release Amount of Drug

An experiment of the in vitro drug release was performed to determine drug delivery efficiency of the nanoparticle prepared in Example 1.

Specifically, after a solution in which the nanoparticles were dispersed was put into the dialysis tube (MWCO 4K), the solution was put into a solution of pH 7.4 (DPBS) and a solution of pH 5.5 (acetate buffer, 10 mM), and then was stirred at 37° C. Thereafter, the solution was skimmed at a scheduled time and lyophilized, and then the solution having the same amount was put therein. 1 ml of an acetonitrile/ distilled water (volume fraction: 75/25) solution was put into the lyophilized solution, and then was refined using a syringe filter. Thereafter, ultra performance liquid chromatography (UPLC; manufactured by Waters Corporation) was operated under a C18 column (Symmetry C18 5 µm 3.9×150 mm column; manufactured by Waters Corporation), and then the release amount of the two drugs according to time was obtained. Here, 1 mL of DPBS/acetonitrile (volume fraction: 50/50) flowed each minute in a mobile phase, and a UV absorption spectrum for detection was set to 230 nm.

Figure 4A:
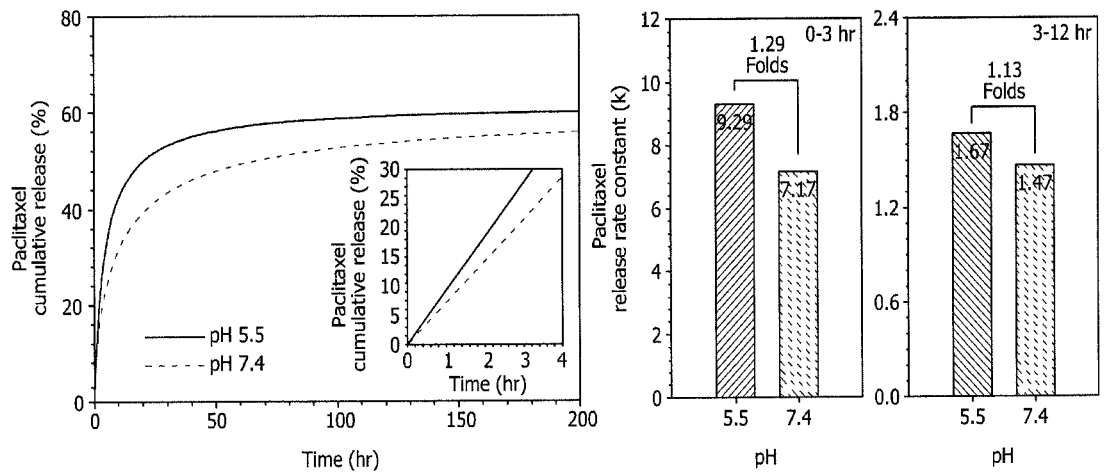
FIG. 4a illustrates an release amount of the drug (left) and an release speed constant (right) of PTX according to pH.
Figure 4B:
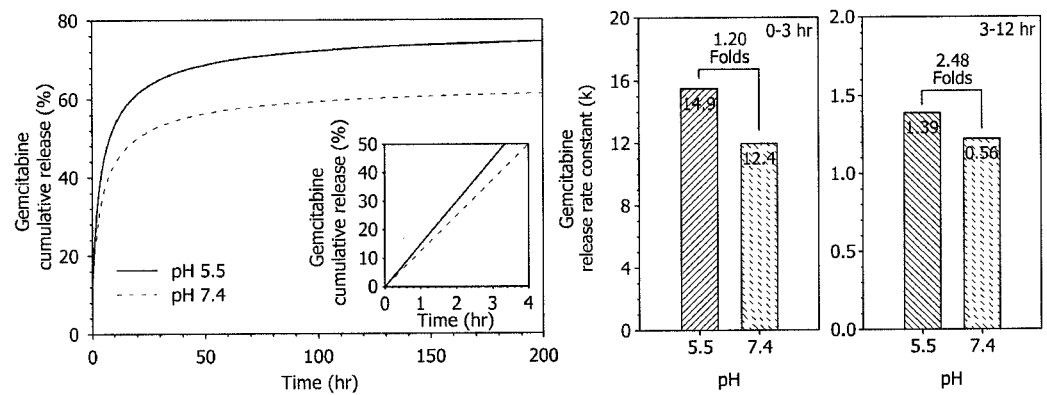
FIG. 4b shows an release amount of the drug (left) and an release speed constant (right) of GEM according to pH.

As a result, as illustrated in FIG. 4, the release speeds of both of the drugs were determined to increase at pH 5.5 (acetic acid buffer 10 mM) with respect to pH 7.4 (DPBS). This denotes that the nanoparticle according to the embodiment of the present invention effectively delivers and releases the drug in a cancer-cell-specific environment.

Experimental Example 3

Determination of Intracellular Introduction of Nanoparticle

In order to determine whether the nanoparticle prepared in Example 1 specifically enters a specific cell by hyaluronic acids, cancer cell strains having a difference in an amount of CD44 over-expression (HuCCT1 which is a CD44 over-expression biliary tract cancer cell strain, and SCK which is a CD44 low expression cholangioma cell strain) were selected, and the amount of CD44 over-expression thereof was determined through flow cytometry.

Specifically, $1 \times 10^6$ HuCCT1 and SCK cells were gathered, and then were cleaned by a blocking buffer including fetal bovine serum at a volume fraction of 0.2% and sodium azide at a volume fraction of 0.02%. Then, anti-mouse CD44 (20 µl) conjugated to isothiocyanate and mouse IgG (20 µl) conjugated to fluorescein isothiocyanate were put therein, and then each was incubated at 4° C. for 30 minutes. Thereafter, the incubated cells were cleaned again by the blocking buffer. After the cells were re-dispersed in a paraformaldehyde solution at a volume fraction of 4% (400 µl), the cells were measured through flow cytometry. As a result, CD44 was determined to be more over-expressed in HuCCT1 which is a biliary tract cancer cell strain than SCK which is a cholangioma cell strain (FIG. 5c).

Further, the cells were analyzed under conditions in which CD44 was blocked and not blocked through confocal laser scanning microscopy using particles labeled with rhodamine B which is a fluorescent material. Specifically, after nanoparticles labeled with rhodamine B (RhoB-MDNCs) were prepared, a cover glass bottom dish in which $2 \times 10^5$ HuCCT1 and SCK cells were absorbed was prepared, and then each nanoparticle was absorbed in the cell for 1.5 hours. Further, after the same amount of the cells were prepared, some of the cells were incubated with an excess amount of hyaluronic acids for 2 hours before the nanoparticles were absorbed in the cells to block CD44, and then the nanoparticles were absorbed in each of the cells in which CD44 was blocked and the cells in which CD44 was not blocked for the same time. After 1.5 hours, a medium was removed, and then the cells were cleaned using DPBS. After the cells were fixed for 30 minutes through a paraformaldehyde solution at a volume fraction of 4%, nuclei were dyed using Hoechst 33258 for 1 hour. Then, fluorescent light was measured through confocal laser scanning microscopy with respect to each experiment.

Figure 5A:
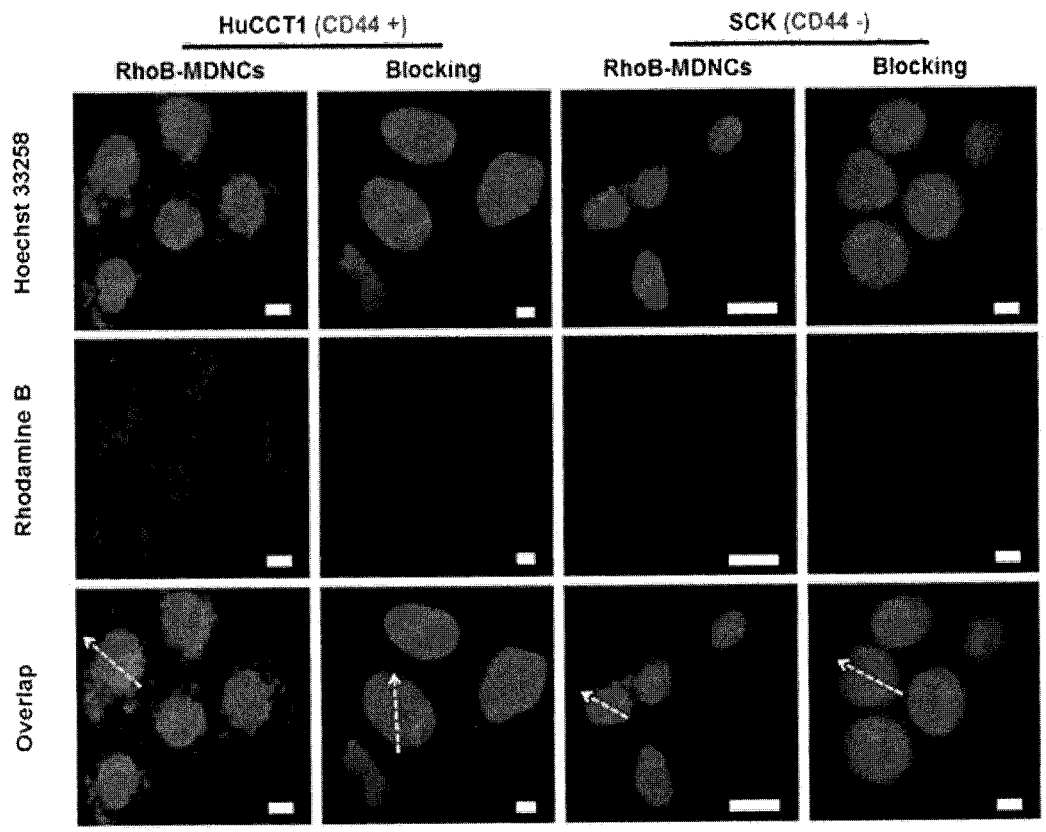
FIG. 5a, FIG. 5b, FIG. 5c and FIG. 5d illustrate the results of the determination of an amount of over-expression of CD44 in two types of cell strains to determine whether the nanoparticle according to the embodiment of the present invention enters the cell well and the degree of intracellular introduction of the nanoparticle in HuccT1(I), HuccT1(II) in which CD44 was blocked.
Figure 5B:
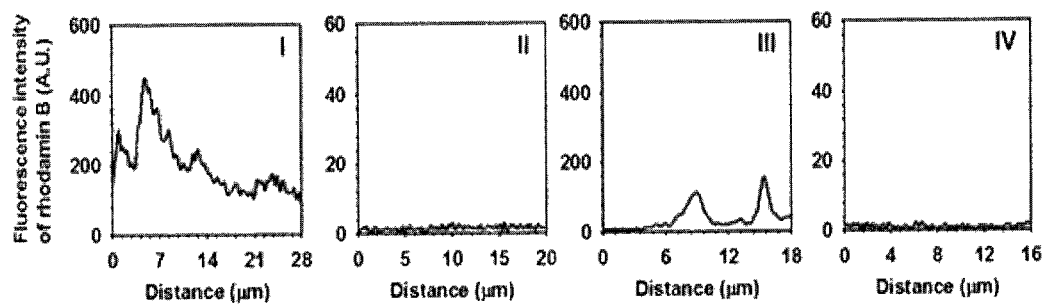
Figure 5C:
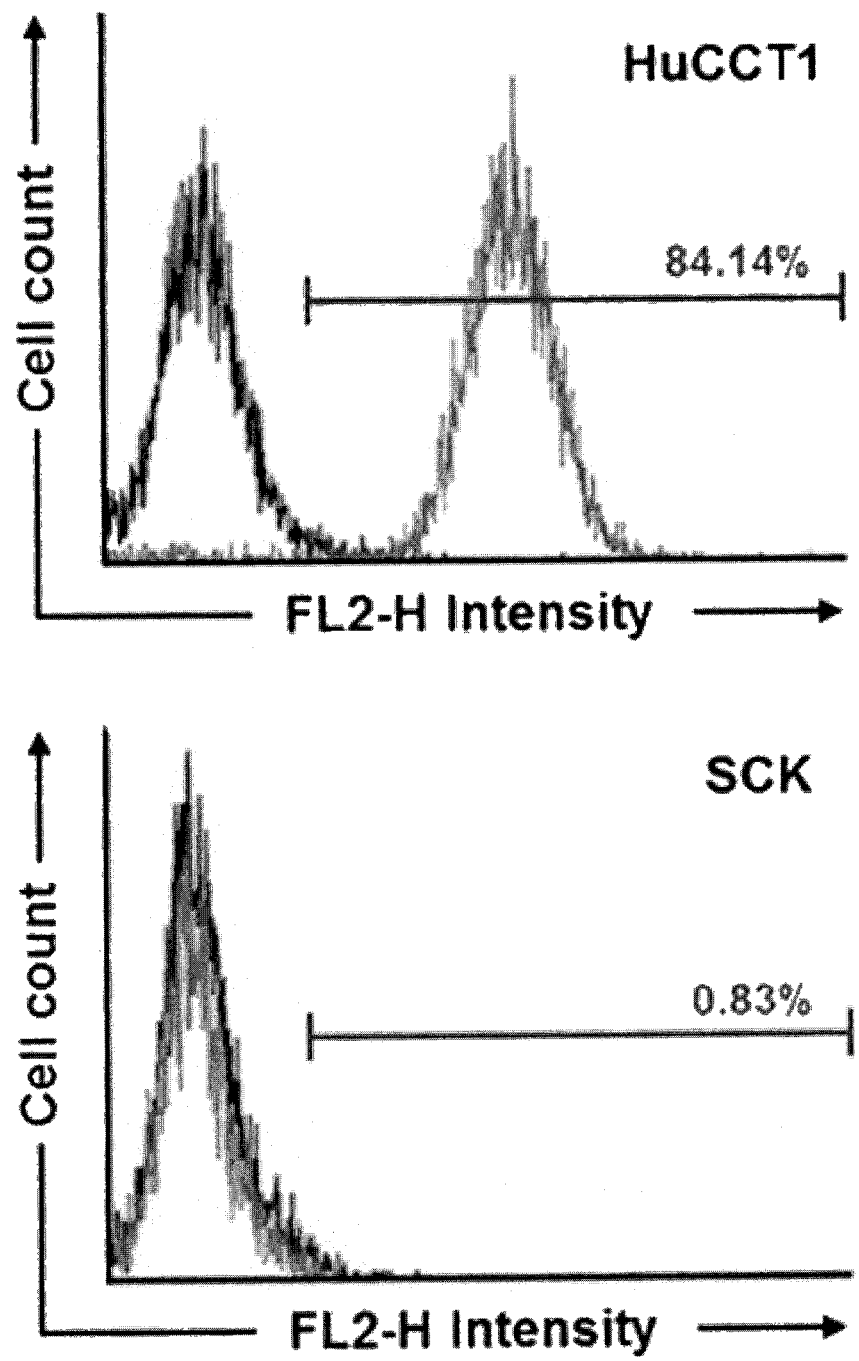

As a result, the particles were determined to enter well in an order of HuCCT1>SCK>SCK blocking CD44=HuCCT1 blocking CD44 (FIG. 5a,b).

Figure 5D:
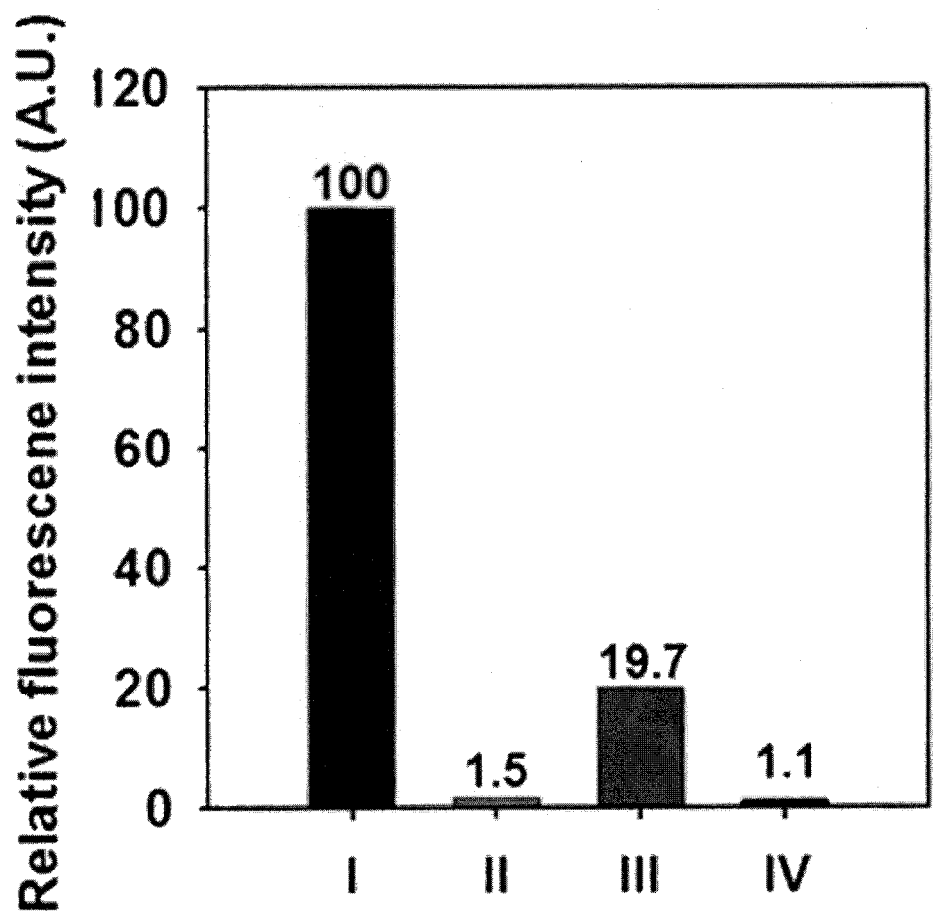
Figure 6A:
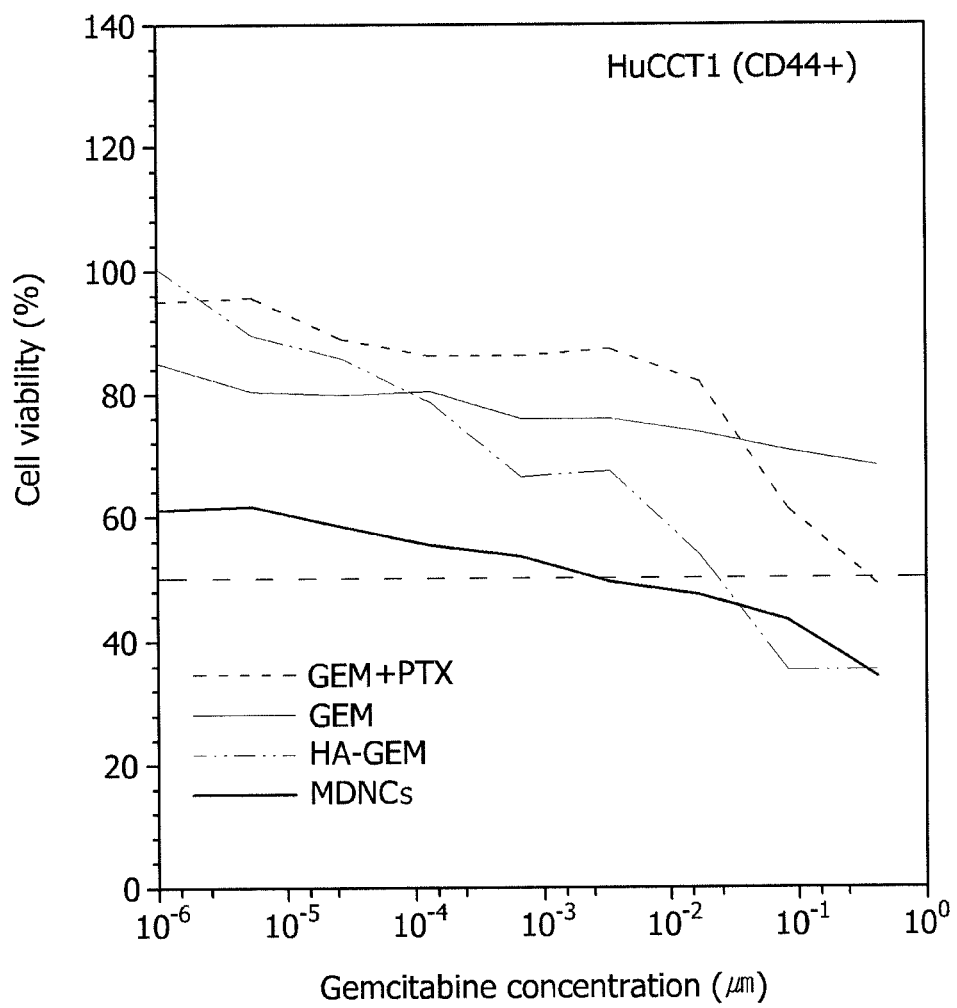
FIG. 6a illustrates the result of the determination of cytotoxicity effects of GEM+PTX, GEM, HA-GEM, and MDNCs according to a concentration of gemcitabine in a HuCCT1 cell strain.
Figure 6B:
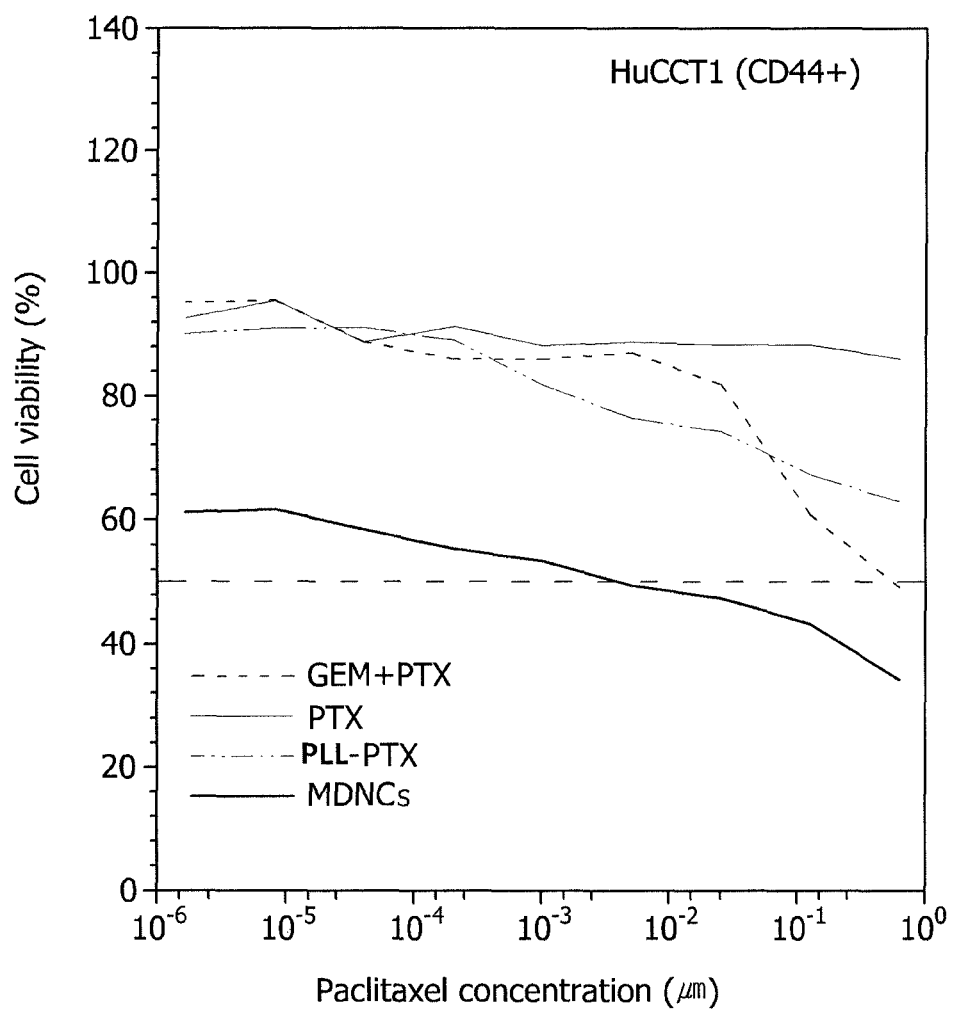
FIG. 6b shows the result of the determination of cytotoxicity effects of GEM+PTX, GEM, HA-GEM, and MDNCs according to the concentration of paclitaxel in the HuCCT1 cell strain.
Figure 6C:
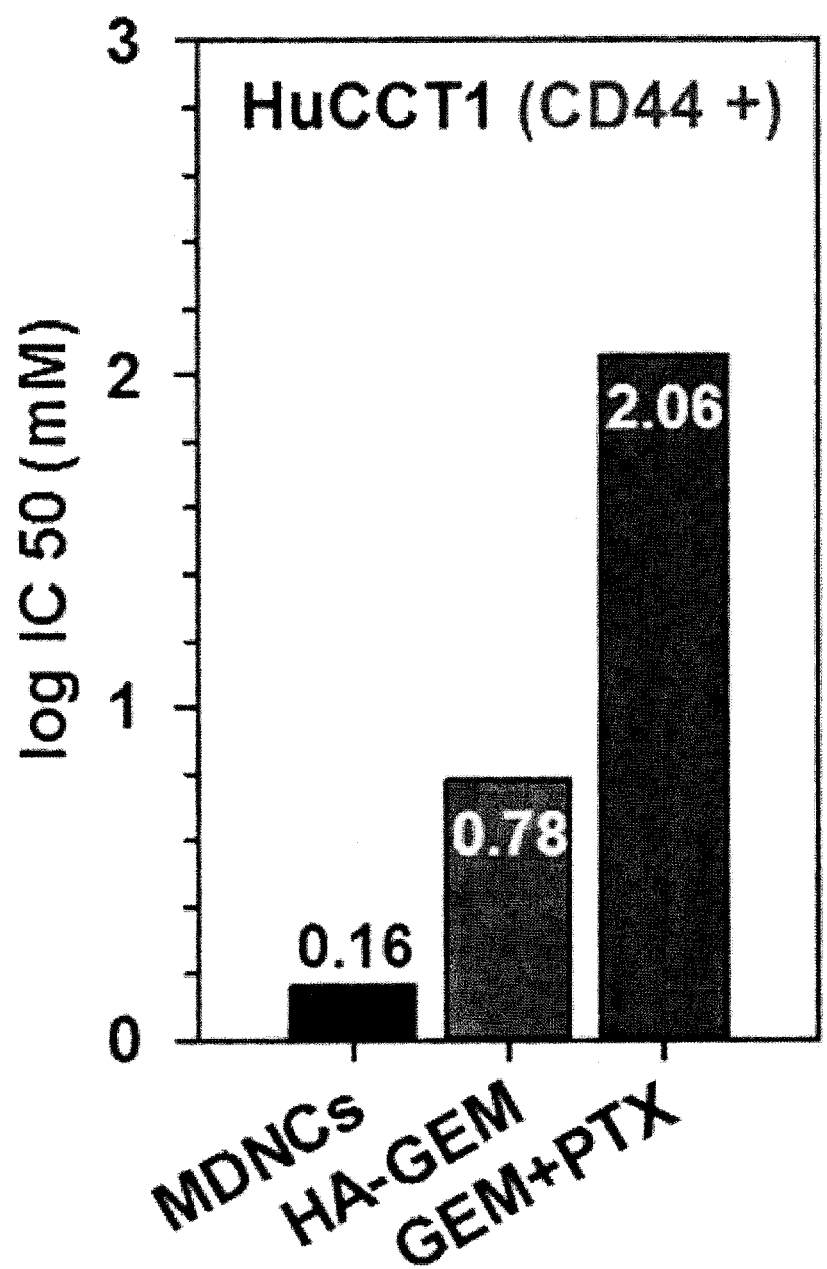
FIG. 6c shows $IC_{50}$ values of GEM+PTX, HA-GEM, and MDNCs in the HuCCT1 cell strain.
Figure 6D:
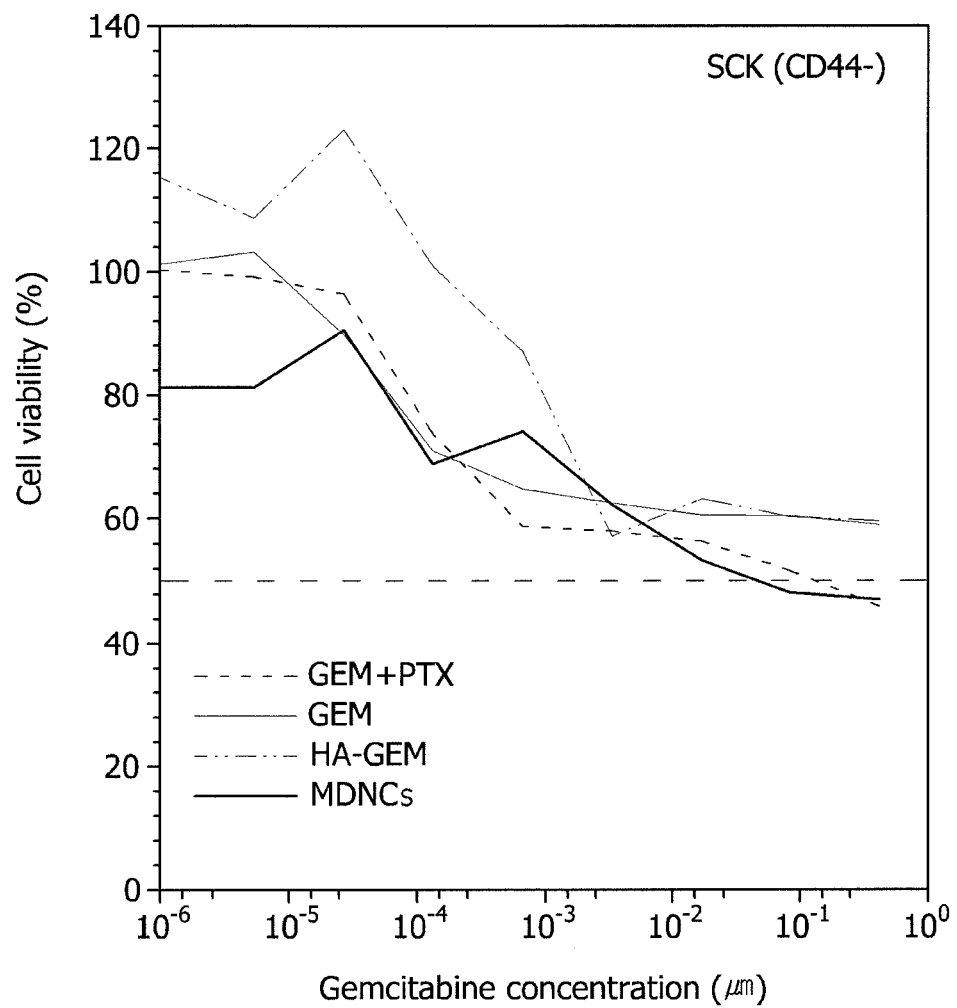
FIG. 6d shows the result of the determination of cytotoxicity effects of GEM+PTX, GEM, HA-GEM, and MDNCs according to the concentration of gemcitabine in an SCK cell strain.
Figure 6E:
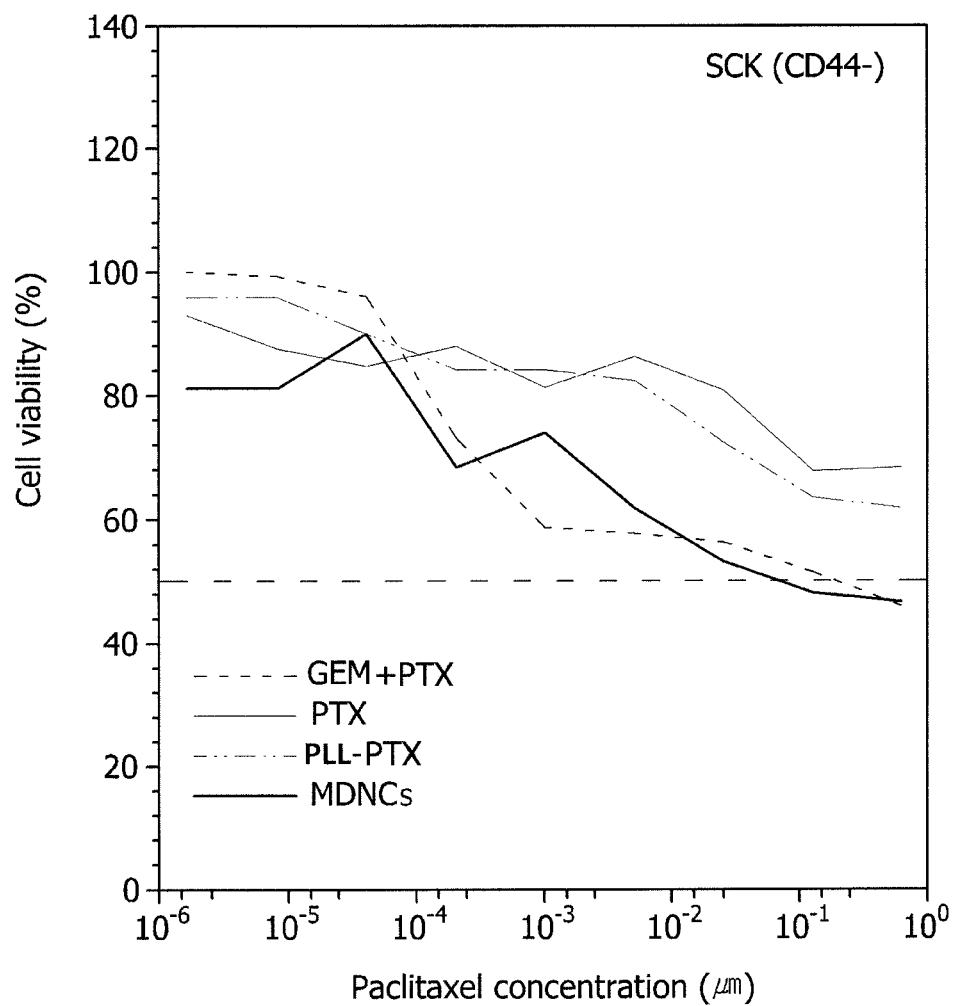
FIG. 6e shows the result of the determination of cytotoxicity effects of GEM+PTX, PTX, PLL-PTX and MDNCs according to the concentration of paclitaxel in the SCK cell strain.
Figure 6F:
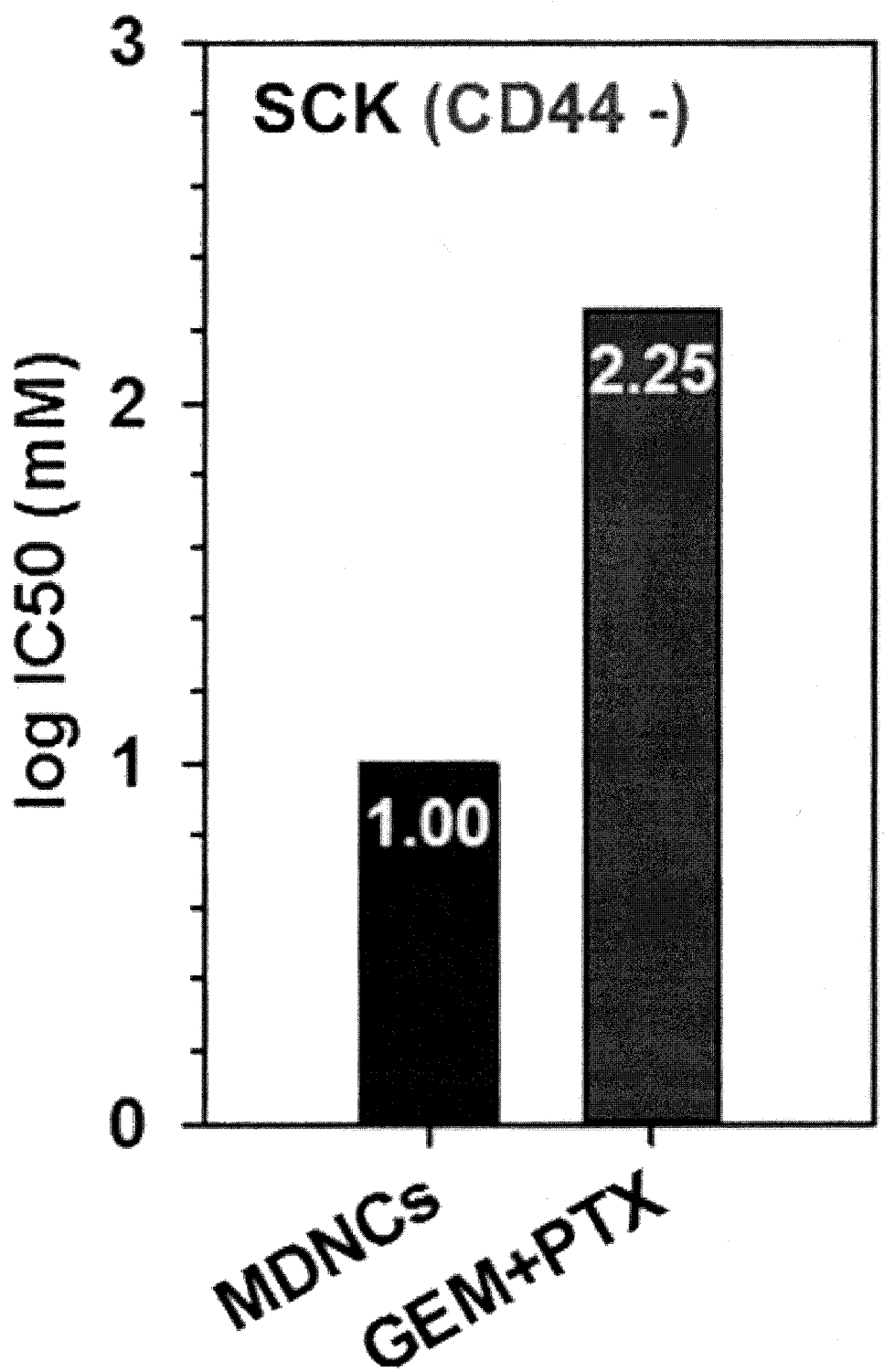
FIG. 6f shows $IC_{50}$ values of GEM+PTX, and MDNCs in the SCK cell strain.

Further, relative fluorescence intensity was calculated according to the following equation and on the basis of the result of the measurement of fluorescence intensity of rhodamine B (FIG. 5d).

$$\text{Relative fluorescence intensity} = \frac{\text{Rhodamine } B \text{ intensity}}{\text{Dash line in } A} \times \frac{1}{RhoB - MDNCs \text{ in } HuCCT1} \quad \text{[Equation 1]}$$

This result supports the fact that the nanoparticle according to the embodiment of the present invention specifically enters a cancer cell in which CD44 is over-expressed.

Experimental Example 4

Determination of Cytotoxic Effect of Nanoparticle

GEM+PTX, GEM, PTX, HA-GEM, PLL-PTX and the nanoparticles (MDNCs) prepared in Example 1 were each treated with HuCCT1 in which CD44 was over-expressed and SCK in which CD44 was low-expressed for 4 hours. GEM+ PTX refers to a group treated with GEM and PTX together, GEM and PTX refer to groups separately treated with GEM and PTX, respectively, HA-GEM refers to a group treated with a complex in which HA and GEM were conjugated, and PLL-PTX refers to a group treated with a complex in which PLL and PTX were conjugated. After the incubation for 24 hours, a cytotoxicity test using an MTT assay was performed. As a result, as illustrated in FIG. 6, MDNCs exhibited $IC_{50}$ values (inhibition dose: 50%) at the lowest concentration, and HA-GEM having a target ability and GEM+PTX treated with the two drugs together sequentially exhibited $IC_{50}$ values in HuCCT1. In the case of SCK, the lowest $IC_{50}$ value was MDNCs, followed by GEM+PTX. The fact that $IC_{50}$ of MDNCs was lower than that of GEM+PTX denotes that an anti-cancer effect of the MENCs according to the embodiment of the present invention is greater than the effect obtained by the treatment with a simple combination of GEM and PTX.

Consequently, when the MDNCs according to the embodiment of the present invention form nanoparticles in which the hydrophobic and the hydrophilic drugs are respectively conjugated to the cationic biocompatible polymer and the anionic biocompatible polymer, it could be determined that each nanoparticle exhibited a greater effect than the combination of the drugs. Further, the intracellular introduction of the MDNCs according to the embodiment of the present invention is performed through CD44, and the case of the cell over-expressing CD44 exhibited an effect 100 times that of the case of the cell low-expressing CD44.

Experimental Example 5

Expression Level of Apoptosis-Inducing Gene of Nanoparticle

The level of expression of an apoptosis gene of each material was compared and analyzed under the same condition as Experimental Example 4.

Specifically, $1 \times 10^6$ HuCCT1 and SCK cells were treated with GEM, PTX, GEM+PTX, HA-GEM, PLL-PTX, HA-GEM, and MDNCs for 4 hours based on the same amount of GEM and PTX. Then, the cells were incubated in a new medium for 24 hours, and thereby the cells were obtained. Total amount of RNA with respect to all the obtained cells was obtained with an RNeasy plus mini kit (QIAGEN Gmbh), and then a concentration of total RNA was obtained using a biophotometer. Thereafter, 2 μg of complementary DNA (cDNA) with respect to the total RNA was synthesized through a high capacity RNA-to-cDNA kit (Applied Biosystems; Thermo Fisher Scientific Inc.). Quantitative analysis of the synthesized cDNA was performed using a QuantiMix SYBR Kit (PKT, Korea) in a real-time PCR system (Light-Cycler 480 System, HNS Bio). The quantitative analysis was performed through a reacting solution (20 μl) including cDNA (1 μl), SYBR Green mixture (10 μl), each of forward primer (1 μl) and reverse primer (1 μl), and DEPC water (7 μl). The used primers were as follows:

```
Bcl-2:
SEQ ID NO: 1:
5'-GT TTC TTC CGG TGT TAG GAG GGG GTC-3'
(forward primer)

SEQ ID NO: 2:
5'-TCC AGG TGT GCA GGT GCC GGT TC-3'
(reverse primer)

Bcl-xL:
SEQ ID NO: 3:
5'-TCC TTG TTT ACG CTT TCC CAC-3'
(forward primer)

SEQ ID NO: 4:
5'-GGT CGC ATT GTG GCC TTT-3'
(reverse primer)

Bax:
SEQ ID NO: 5:
5'-T TCT GGA GAG CCC CCC TCA-3'
(forward primer)

SEQ ID NO: 6:
5'-CAA AAG TAG AAA AGG GCC GAC AA-3'
(reverse primer)

GAPDH:
SEQ ID NO: 7:
5'-CT TGT CCT CCT CGT CTC TCG-3'
(forward primer)

SEQ ID NO: 8:
5'-TGA CTC CGA CCT TCA CCT TC-3'
(reverse primer).
```

PCR was performed at 95° C. for 5 minutes, and then genes were amplified for 45 cycles (10 seconds at 95° C., 10 seconds at 60° C., and 10 seconds at 72° C.). A relative amount of each mRNA was analyzed using a Ct method (2-ΔΔCt) based on GAPDH of each cell, from data obtained as described above.

Figure 7A:
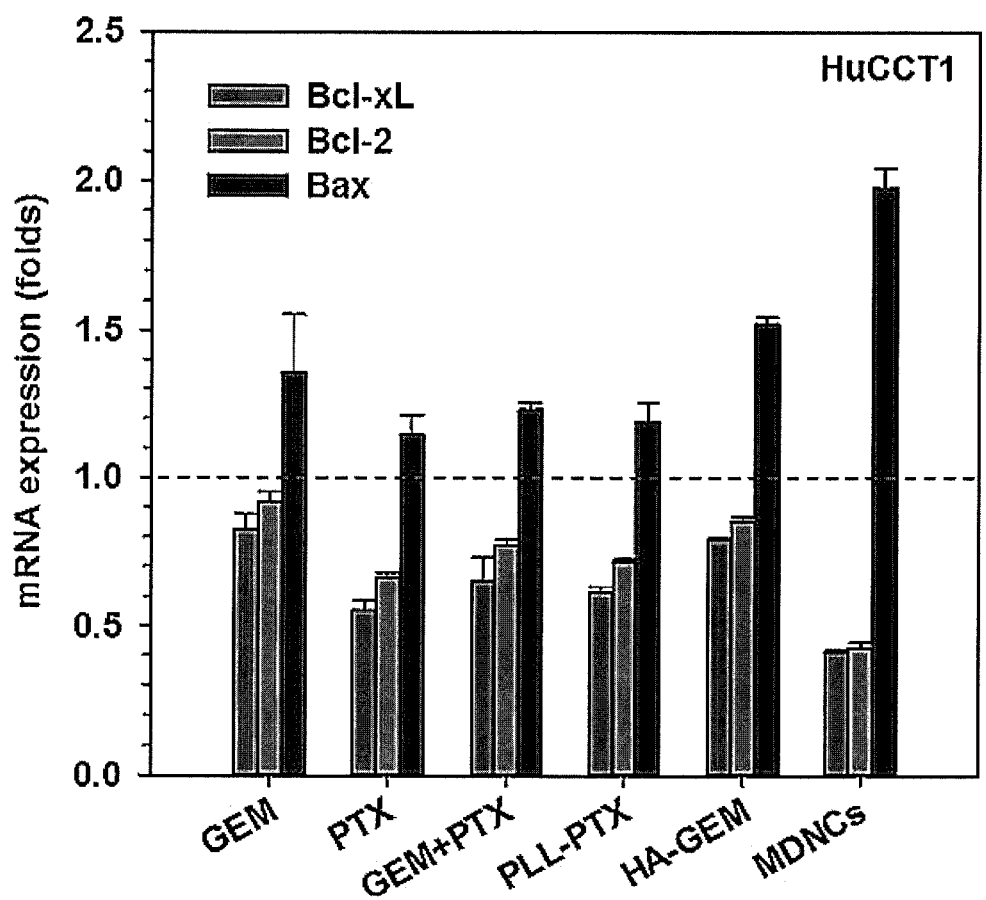
FIG. 7a illustrates the level of expression of an apoptosis-related gene in mRNA in GEM+PTX, GEM, PTX, HA-GEM, PLL-PTX and MDNCs groups in the HuCCT1 cell strain.
Figure 7B:
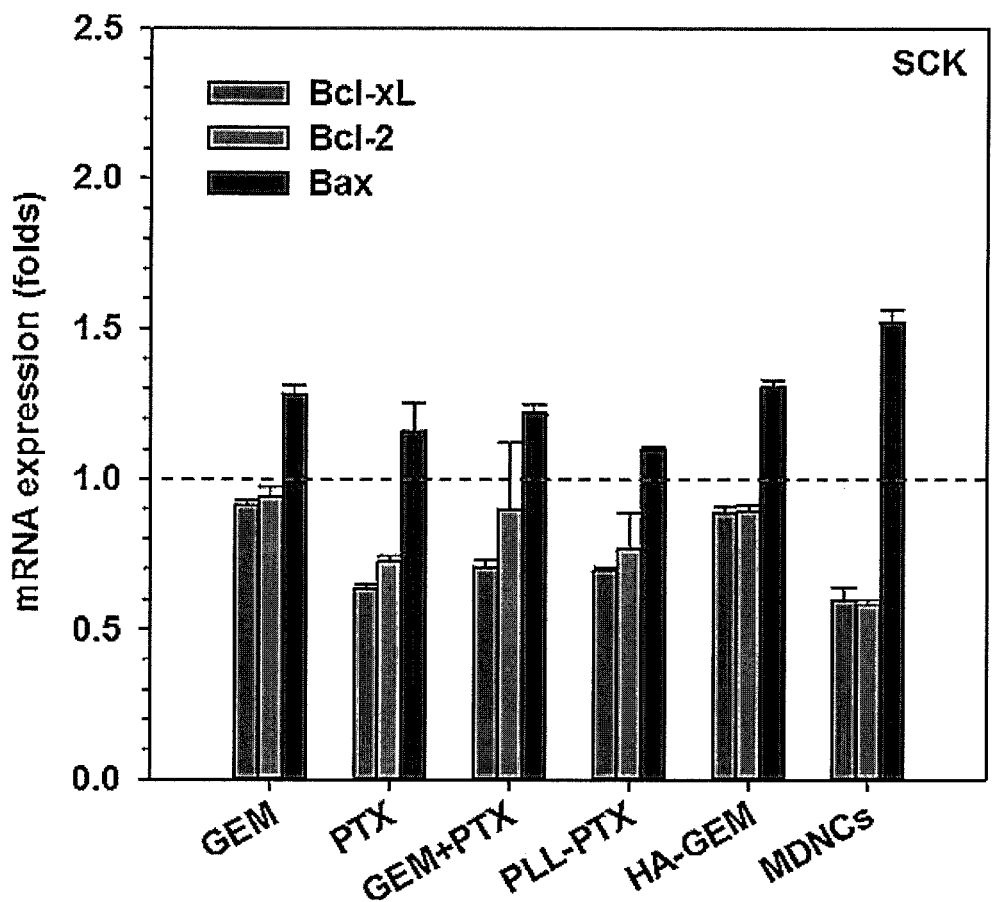
FIG. 7b shows the level of mRNA expression of an apoptosis-related gene in GEM+PTX, GEM, PTX, HA-GEM, PLL-PTX and MDNCs groups in the SCK cell strain.

As a result, in the case of MDNCs, it was determined that Bax which is an apoptosis-inducing gene was over-expressed in the HuCCT1 cell over-expressing CD44 as compared to the SCK cell low-expressing CD44. Further, it was determined that Bcl-x1 and Bcl-2 which are apoptosis-suppressing genes were low-expressed. Further, when the same amount of drugs were treated, groups of the drugs which were not in the form of the particles, that is, GEM, PTX, GEM+PTX, and PLL-PTX groups, had few changes according to the level of expression of CD44, and effects thereof were lower than those of the MDNCs (FIG. 7a, b).

Figure 7C:
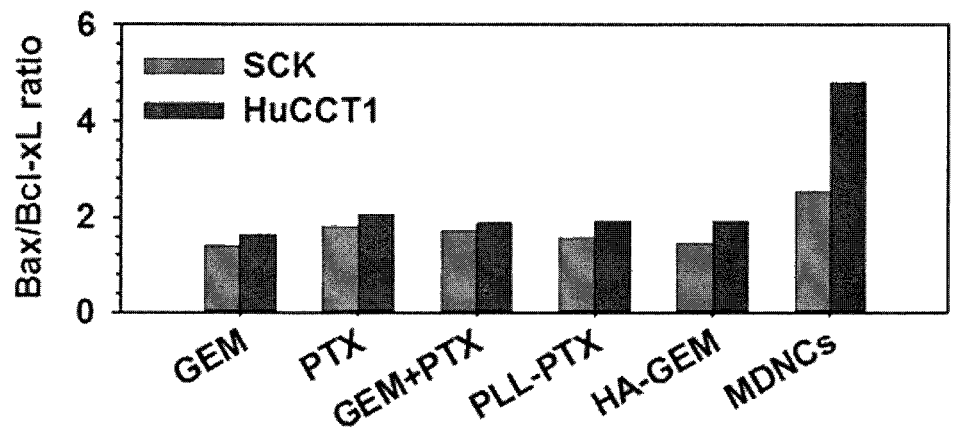
FIG. 7c and FIG. 7d show an expression ratio of the apoptosis-related gene in each group according to the HuccT1 and SCK cell strains.
Figure 7D:
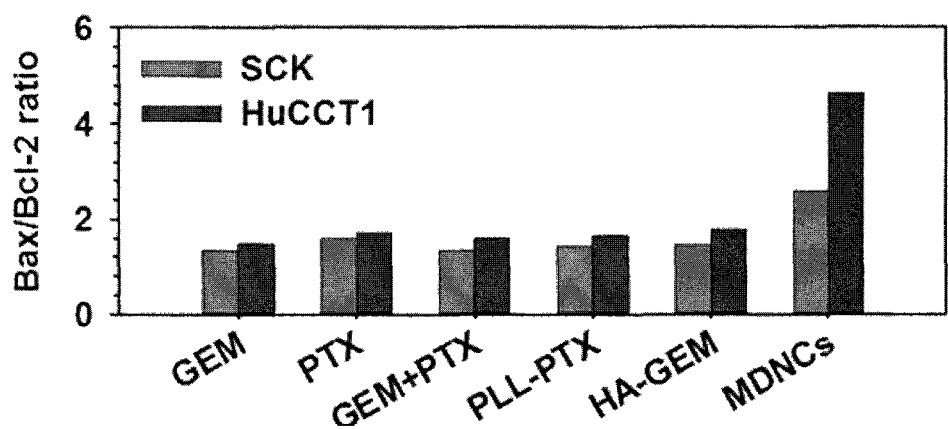

Further, when Bax/Bcl-2 and Bax/Bcl-x1 values through which the degree of apoptosis may be determined were compared, the apoptosis effect of the MDNCs was determined to be more excellent than those of other groups (FIG. 7c, d).

Experimental Example 6

Effect of Suppressing Cancer Cell Proliferation of Nanoparticle (In Vivo)

In order to determine an effect of suppressing the cancer cell proliferation of the nanoparticle according to the embodiment of the present invention, 200 μl of RPMI1640 including HuCCT1 cells ($5\times10^6$) was injected into BALB/c male nude mice (4 weeks).

Then, cancer cells were proliferated for 12 days, 100 μl of saline, HA-GEM, GEM+PTX, and MPDNCs were injected through tail veins twice over two weeks at an interval of one week. Thereafter, sizes of the cancer cells and weights of the mice were determined at intervals of 3 days.

The result thereof is shown in FIG. 8. As a result of determining a relative change of the size of the cancer cells, when the drug was delivered by the MPDNCs, the sizes of the cancer cells were determined to decrease (FIG. 8a). As the result of the weight measurement, there was little change in the weights in all the groups, and thus it was determined that states of mice were maintained well without any change except for the drug treatment (FIG. 8b).

Figure 8A:
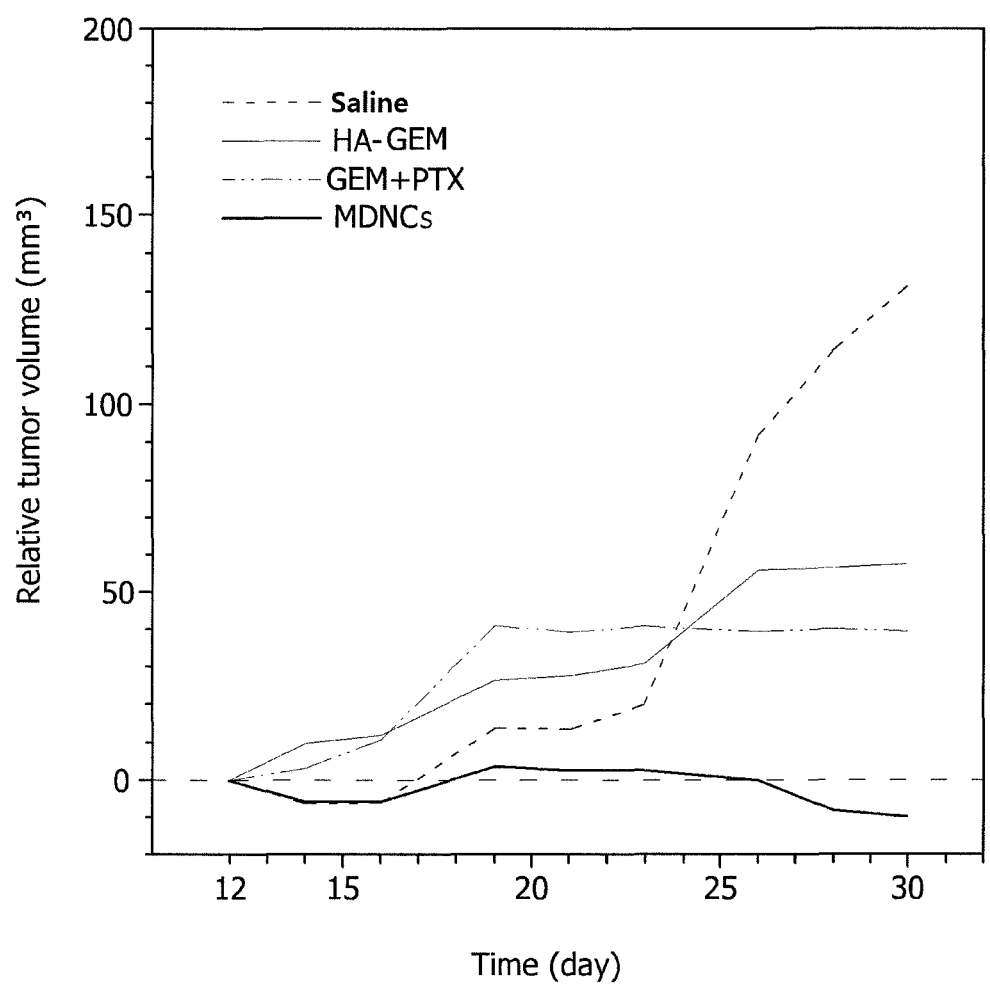
FIG. 8a, FIG. 8b, FIG. 8c, FIG. 8d and FIG. 8e illustrate the results of the determination of an effect of suppressing cancer cell proliferation of the nanoparticle according to the embodiment of the present invention.
Figure 8B:
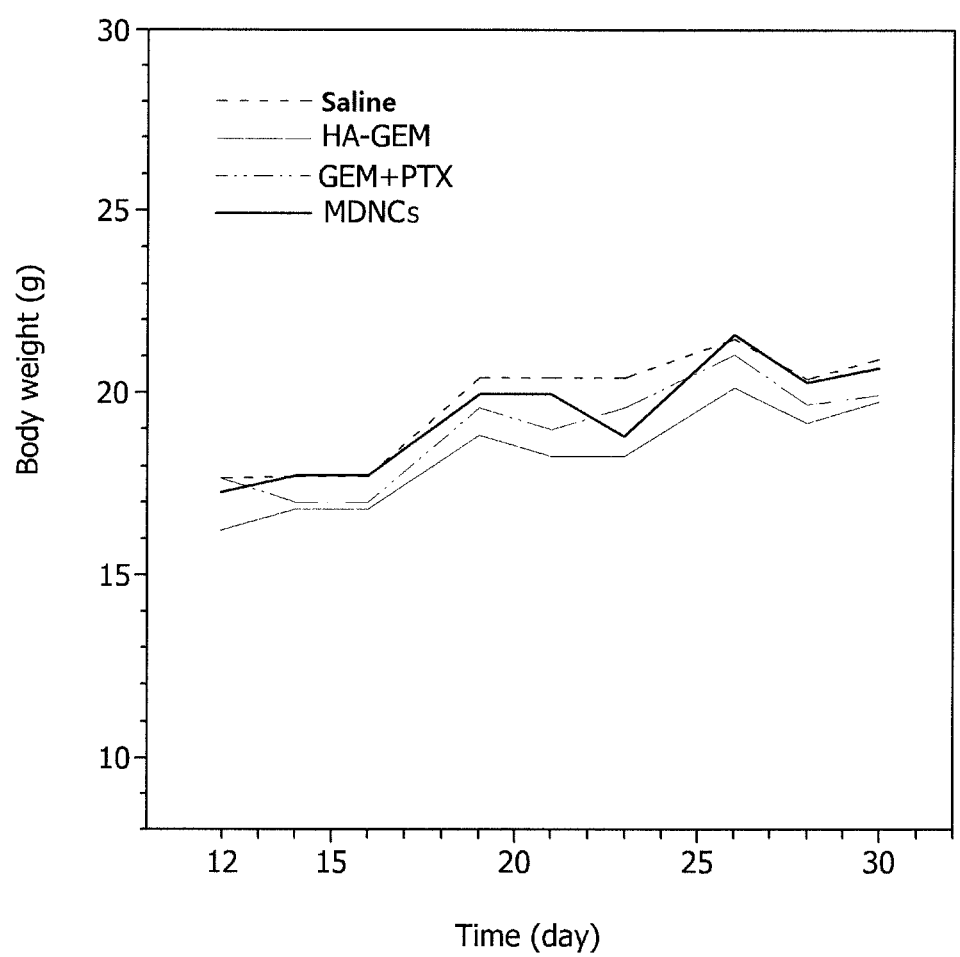
Figure 8C:
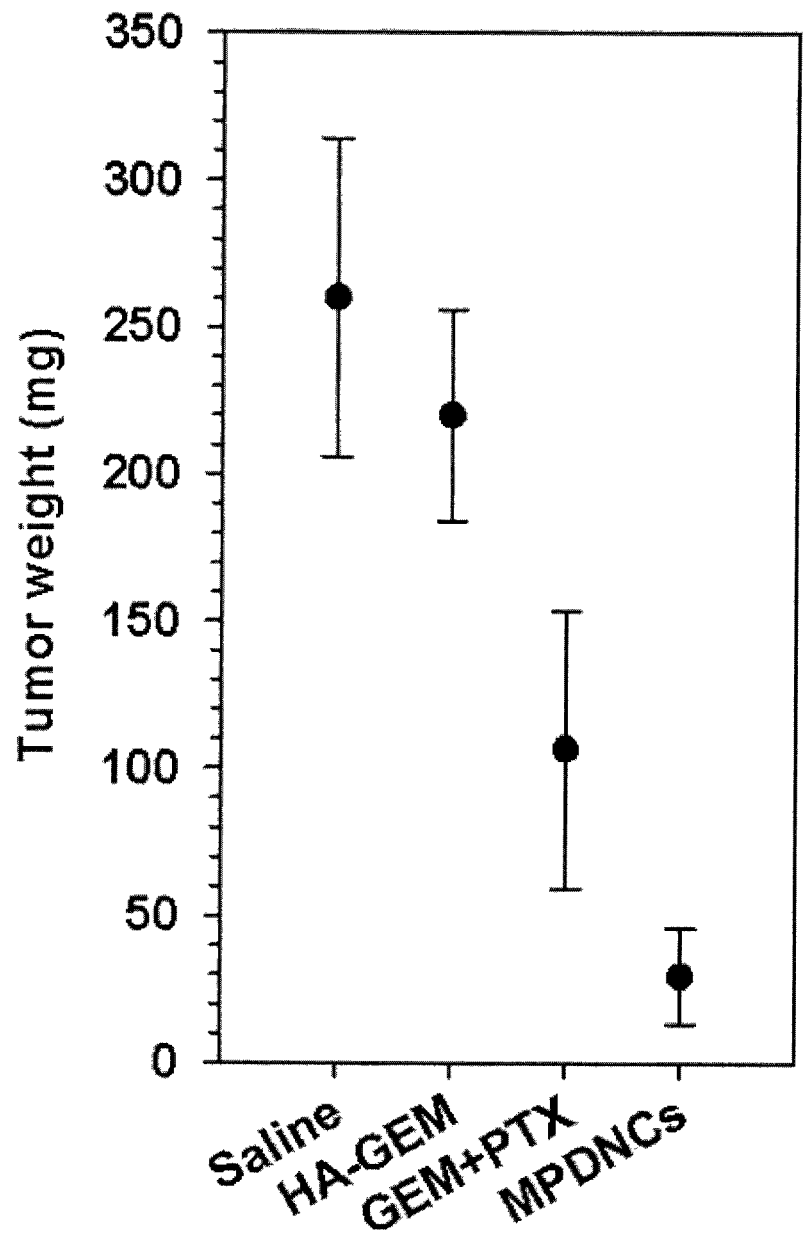
Figure 8D:
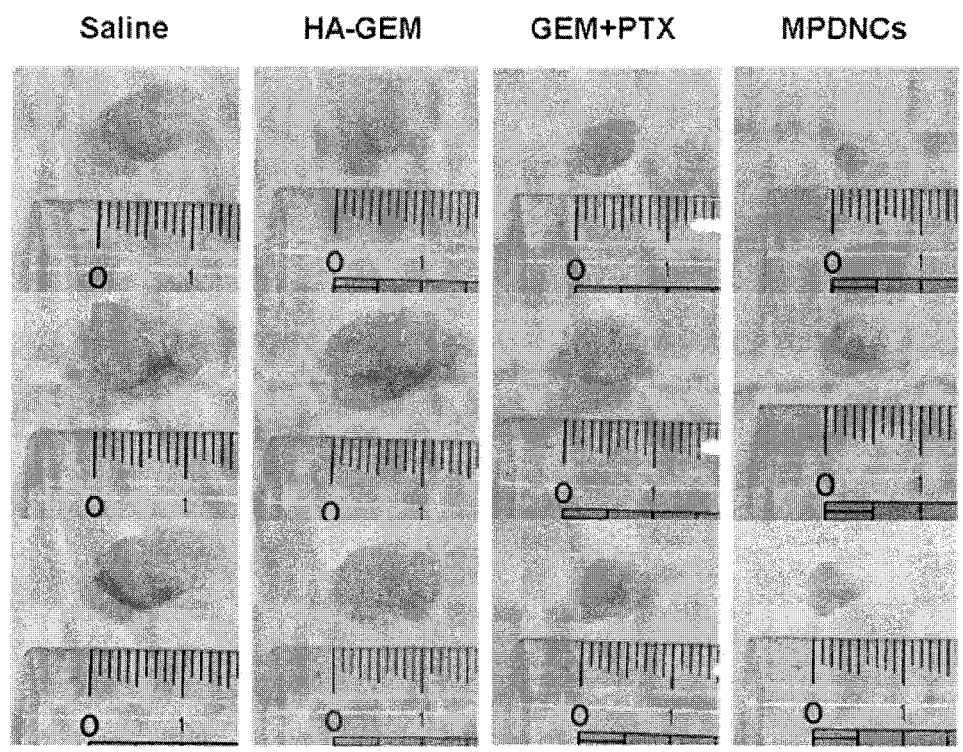

Further, on the thirtieth day, a section of cancer tissue was cut, and the weight of the cut cancer section was measured (FIG. 8c). FIG. 8d shows the cut section of cancer tissue (FIG. 8d).

Figure 8E:
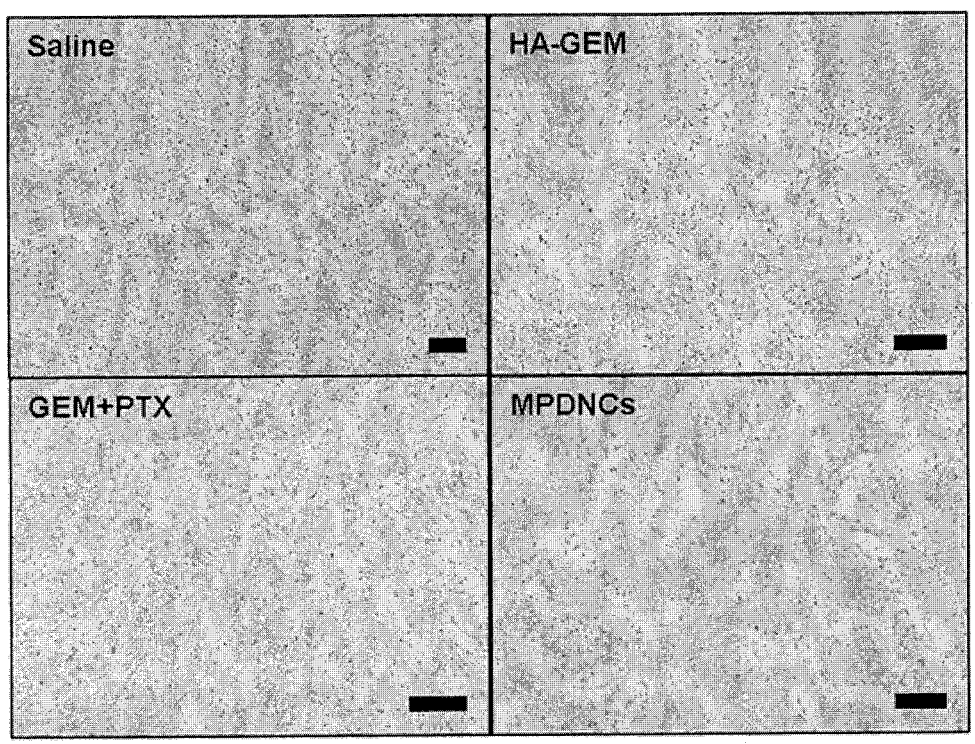

Further, histological analysis was performed through H&E staining using a virtual microscope. As a result, it was determined that the stained sites were smallest when the drugs were delivered by the MPDNCs (FIG. 8e).

These results show that the MPDNCs according to the embodiment of the present invention have an excellent effect of suppressing cancer cell proliferation by controlling the release of the drug as compared to the cases in which the treatment of each of the hydrophilic drug and the hydrophobic drug is separately performed, or a combination of the two drugs is used.

What is claimed is:

1. A nanoparticle comprising a hydrophobic drug conjugated to a cationic biocompatible polymer and a hydrophilic drug conjugated to an anionic biocompatible polymer, and forming a self-assembly by a balance between a cation and an anion,
  wherein the anionic biocompatible polymer is hyaluronic acid, wherein the cationic biocompatible polymer is one or more selected from the group consisting of polylysine, polyhistidine, and polyarginine,
  wherein the hydrophobic drug is one or more selected from the group consisting of vinblastine, etoposide, alkeran, cytoxan, daunorubicin, hydrea, mithramycin, mitomycin, mitoxantrone, nitrogen mustard, velban, vincristine, carboplatinum, idarubicin, irinotecan, leustatin, navelbine, taxotere, topotecan, adriamycin, daunomycin, and paclitaxel,
  and wherein the hydrophilic drug is one or more selected from the group consisting of busulfan, chlorambucil, cyclophosphamide, melphalan, cisplatin, ifosfamide, cytarabine, 5-fluorouracil (5-FU), methotrexate (MTX), actinomycin D, bleomycin, and gemcitabine
  wherein conjugation between the hydrophobic drug and the cationic biocompatible polymer occurs through an ester, imine, hydrazone, acetal, or cyclic acetal linkage,
  and wherein conjugation between the hydrophilic drug and the anionic biocompatible polymer occurs through an ester, imine, hydrazone, acetal, or cyclic acetal linkage.

2. The nanoparticle of claim 1, wherein the linkage between the cationic biocompatible polymer and the hydrophobic drug, or the linkage between the hyaluronic acid and the hydrophilic drug is cut in a pH range of 5.0 to 5.5 in cancer cells.

3. The nanoparticle of claim 1, wherein the nanoparticle is bio-environment-sensitive and has an average diameter in a range of 100 to 300 nm.

4. The nanoparticle of claim 1, wherein a weight ratio of a hydrophobic drug conjugated to a cationic biocompatible polymer and a hydrophilic drug conjugated to an anionic biocompatible polymer is in a range of 1:70 to 70:1.

5. A drug carrier comprising the nanoparticle of claim 1.

6. A method of preparing the nanoparticle of claim 1, comprising:
  providing a cationic biocompatible polymer selected from the group consisting of polylysine, polyhistidine, and polyarginine conjugated via an ester, imine, hydrazone, acetal, or cyclic acetal linkage to a hydrophobic drug selected from the group consisting of vinblastine, etoposide, alkeran, cytoxan, daunorubicin, hydrea, mithramycin, mitomycin, mitoxantrone, nitrogen mustard, velban, vincristine, carboplatinum, idarubicin, irinotecan, leustatin, navelbine, taxotere, topotecan, adriamycin, daunomycin, paclitaxel, and combinations thereof;
  providing hyaluronic acid conjugated via an ester, imine, hydrazone, acetal, or cyclic acetal linkage to a hydrophilic drug selected from the group consisting of busulfan, chlorambucil, cyclophosphamide, melphalan, cisplatin, ifosfamide, cytarabine, 5-fluorouracil (5-FU), methotrexate (MTX), actinomycin D, bleomycin, and gemcitabine; and
  reacting the hydrophobic drug conjugated to a cationic biocompatible polymer and the hydrophilic drug conjugated to an anionic biocompatible polymer to form a nanoparticle.

7. A method of treating cancer, comprising administering the drug carrier of claim 5 to an individual who has cancer.

8. The method of treating cancer of claim 7, wherein the cancer is pancreatic cancer, liver cancer, breast cancer, lung cancer, stomach cancer, rectal cancer, gallbladder cancer, ovarian cancer, bladder cancer, colon cancer, lymphoma, brain cancer, uterine cancer, prostate cancer and a malignant melanoma or biliary tract cancer.

* * * * *

SEQUENCE LISTING

<160> NUMBER OF SEQ ID NOS: 8

<210> SEQ ID NO 1
<211> LENGTH: 26
<212> TYPE: DNA
<213> ORGANISM: Artificial
<220> FEATURE:
<223> OTHER INFORMATION: Bcl-2 forward primer

<400> SEQUENCE: 1
gtttcttccg gtgttaggag ggggtc                                         26

<210> SEQ ID NO 2
<211> LENGTH: 23
<212> TYPE: DNA
<213> ORGANISM: Artificial
<220> FEATURE:
<223> OTHER INFORMATION: Bcl-2 reverse primer

<400> SEQUENCE: 2
tccaggtgtg caggtgccgg ttc                                            23

<210> SEQ ID NO 3
<211> LENGTH: 21
<212> TYPE: DNA
<213> ORGANISM: Artificial
<220> FEATURE:
<223> OTHER INFORMATION: Bcl-xL forward primer

<400> SEQUENCE: 3
tccttgttta cgctttccca c                                              21

<210> SEQ ID NO 4
<211> LENGTH: 18
<212> TYPE: DNA
<213> ORGANISM: Artificial
<220> FEATURE:
<223> OTHER INFORMATION: Bcl-xL reverse primer

<400> SEQUENCE: 4
ggtcgcattg tggcctttt                                                 18

<210> SEQ ID NO 5
<211> LENGTH: 19
<212> TYPE: DNA
<213> ORGANISM: Artificial
<220> FEATURE:
<223> OTHER INFORMATION: Bax forward primer

<400> SEQUENCE: 5
ttctggagag ccccctca                                                  19

<210> SEQ ID NO 6
<211> LENGTH: 23
<212> TYPE: DNA
<213> ORGANISM: Artificial
<220> FEATURE:
<223> OTHER INFORMATION: Bax reverse primer

<400> SEQUENCE: 6
caaaagtaga aagggccga caa                                             23

<210> SEQ ID NO 7
<211> LENGTH: 20
<212> TYPE: DNA
<213> ORGANISM: Artificial
<220> FEATURE:
<223> OTHER INFORMATION: GAPDH forward primer

<400> SEQUENCE: 7
cttgtcctcc tcgtctctcg                                                20

<210> SEQ ID NO 8
<211> LENGTH: 20
<212> TYPE: DNA

```
<213> ORGANISM: Artificial
<220> FEATURE:
<223> OTHER INFORMATION: GAPDH reverse primer

<400> SEQUENCE: 8
tgactccgac cttcaccttc                                              20
```